(12) United States Patent
Morrissey

(10) Patent No.: US 9,682,090 B2
(45) Date of Patent: Jun. 20, 2017

(54) METHODS FOR TREATING AND PREVENTING PROSTATE CANCER BONE METASTASES

(71) Applicant: University of Washington, Seattle, WA (US)

(72) Inventor: Colm Morrissey, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/941,281

(22) Filed: Nov. 13, 2015

(65) Prior Publication Data

US 2016/0136189 A1 May 19, 2016

Related U.S. Application Data

(60) Provisional application No. 62/079,698, filed on Nov. 14, 2014.

(51) Int. Cl.
*A61K 31/662* (2006.01)
*A61K 31/00* (2006.01)

(52) U.S. Cl.
CPC ............ *A61K 31/662* (2013.01); *A61K 31/00* (2013.01)

(58) Field of Classification Search
CPC .............................. A61K 31/66; A61K 31/662
USPC ........................................................ 514/114
See application file for complete search history.

(56) References Cited

U.S. PATENT DOCUMENTS

| | | | |
|---|---|---|---|
| 5,780,455 A | 7/1998 | Brenner et al. | |
| 7,148,210 B2 * | 12/2006 | Abraham ........... | A61K 31/7076 514/79 |
| 2011/0065672 A1 | 3/2011 | Kirschenbaum et al. | |

OTHER PUBLICATIONS

Prostate, 1987; 10(1): 69-77, Shao et al., abstract.*
Prostate, 1987; 10(1): 69-77, Shao et al., full document.*
Ariizumi et al., "Expression of podoplanin in human bone and bone tumors: New marker of osteogenic and chondrogenic bone tumors," PathoIInt 60, Nov. 10, 2009, pp. 193-202.
Bagnato et al. "Role of the endothelin axis and its antagonists in the treatment of cancer," Br J Pharmacol, Jan. 2, 2011, 163, pp. 220-233.
Beers et al., "Phosphatase inhibitors—III. Benzylaminophosphonic acids as potent inhibitors of human prostatic acid phosphatase," Bioorg Med Chem 4(10), Jun. 24, 1996, pp. 1693-1701.
Bijsterbosch et al., "Association study of candidate genes for the progression of hand osteoarthritis," Jan. 18, 2013, Osteoarthritis Cartilage 21, pp. 565-569.
Billiard et al., "The orphan receptor tyrosine kinase Ror2 modulates canonical Wnt signaling in osteoblastic cells," Mol Endocrinol19(1), Jan. 2005, pp. 90-101.

Bubendorf et al., "Metastatic patterns of prostate cancer: an autopsy study of 1,589 patients," Hum Pat, 2000, pp. 578-583 hoi 31.
Chen et al., "Synergistic inhibition of Wnt pathway by HIF-1alpha and osteoblast-specific transcription factor osterix (Osx) in osteoblasts," PLoS One 7:e5294S, Dec. 27, 2012, 7 pages.
Chuang et al., "Human prostatic acid phosphatase, an authentic tyrosine phosphatase, dephosphorylates ErbB-2 and regulates prostate cancer cell growth," J Bio Chem 285, May 24, 2010, pp. 23598-23606.
Clarkin et al., "VEGF and bone cell signalling: an essential vessel for communication?" Cell Biochem Funct 31, Nov. 5, 2012, pp. 1-11.
Dhodapkar et al., "Syndecan-1 is a multifunctional regulator of myeloma pathobiology: control of tumor cell survival, growth, and bone cell differentiation," Blood 91(8), Apr. 15, 1998, pp. 2679-2688.
Erlandsen et al., "Pleiotrophin expression during odontogenesis," J Histochem Cytochem 60, Jan. 10, 2012, pp. 366-375.
Feeley et al. "Influence of BMPs on the formation of osteoblastic lesions in metastatic prostate cancer," J Bone Miner Res, Aug. 1, 2005, 20(12), pp. 2189-2199.
Fizazi et al., "Oenosumab versus zoledronic acid for treatment of bone metastases in men with castration-resistant prostate cancer: a randomised, double-blind study," Lancet, Mar. 5, 2011, 377(9768) pp. 813-822.
Genetos et al., "Betacellulin inhibits osteogenic differentiation and stimulates proliferation through HIF-1alpha," Cell Tissue Res , Feb. 18, 2010, 340, pp. 81-89.
Gross et al., "A phase II trial of docetaxel and erlotinib as first-line therapy for elderly patients with androgen-independent prostate cancer," BMC Cancer 7:142, Jul. 27, 2007, 6 pages.
Ishibe et al., "Human prostatic acid phosphatase directly stimulates collagen synthesis and alkaline phosphatase content of isolated bone cells," J Clin Endocrinol Metab, 1991, 73(4) pp. 785-792.
Jin et al., "Steps in prostate cancer progression that lead to bone metastasis," Int J Cancer (2011) 128, pp. 2545-2561.
Kawai et al., "Zinc-finger transcription factor odd-skipped related 2 is one of the regulators in osteoblast proliferation and bone formation," J Bone Miner Res 22(9), Jun. 4, 2007, pp. 1362-1372.
Kim et al. "Betacellulin induces angiogenesis through activation of mitogen-activated protein kinase and phosphatidylinositol3'-kinase in endothelial cell," FASEB J, Dec. 3, 2002, 17, pp. 318-320.

(Continued)

*Primary Examiner* — Yong Chu
*Assistant Examiner* — Sonya Wright
(74) *Attorney, Agent, or Firm* — Stoel Rives LLP; Zhi-Xiang (Alex) Oh

(57) ABSTRACT

Methods for treating a subject having a prostate cancer bone metastasis are disclosed. Methods for prophylactically treating a subject at risk of developing a prostate cancer bone metastasis are also disclosed. The methods for treating a subject having, or at risk of developing, a prostate cancer bone metastasis may include administering a prostatic acid phosphatase inhibiting agent to the subject. The methods for treating a subject having, or at risk of developing, a prostate cancer bone metastasis may also include administering a phosphonic acid to the subject. Further, the phosphonic acid may include a benzylaminophosphonic acid, such as [phenyl[(phenylmethyl)amino]methyl]-phosphonic acid).

17 Claims, 12 Drawing Sheets

(56) References Cited

OTHER PUBLICATIONS

Kirschenbaum et al., "Prostatic acid phosphatase is expressed in human prostate cancer bone metastases and promotes osteoblast differentiation," Ann N Y Acad Sci, 2011, 1237, pp. 64-70.

Kuroda C et al., "Distribution, gene expression, and functional role of EphA4 during ossification," Biochem Biophys Res Commun 374, Jul. 2, 2008, pp. 22-27.

Larson et al "Characterization of osteoblastic and osteolytic proteins in prostate cancer bone metastases," Prostate, Jun. 2013, 73(9), pp. 932-940.

Larson et al., "Prostate cancer derived prostatic acid phosphatase promotes an osteoblastic response in the bone microenvironment," Clin Exp Metastasis, Feb. 2014, 31(2), pp. 247-256.

Lee et al, "Treatment and prevention of bone complications from prostate cancer," Bone, Jan. 2011, 48(1), pp. 88-95.

Lin et al., "A 45-kDa ErbB3 secreted by prostate cancer cells promotes bone formation," Oncogene 27(39), Sep. 4, 2008, pp. 5195-5203.

Lisignoli et al., "CCL20/CCR6 chemokine/receptor expression in bone tissue from osteoarthritis and rheumatoid arthritis patients: different response of osteoblasts in the two groups," J Cell Physiol 221, Apr. 21, 2009, pp. 154-160.

Metz-Estrella et al., "TRIP-1: a regulator of osteoblast function," J Bone Miner Res 27(7), Jul. 2012, pp. 1576-1584.

Monroe et al., "Update on Wnt Signaling in bone cell biology and bone disease," Gene 492, Jan. 15, 2012, pp. 1-18.

Morrissey et al., "Effects of androgen deprivation therapy and bisphosphonate treatment on bone in patients with metastatic castration-resistant prostate cancer: results from the University of Washington," Feb. 2013, Rapid Autopsy Series. 1 Bone Miner Res 28(2), pp. 333-340.

Muniyan et al., "Human prostatic Acid phosphatase: structure, function and regulation," IntJ Mol Sci 14, May 21, 2013, pp. 10438-10464.

Neto et al., "Profiling the changes in signaling pathways in ascorbic add/beta-glycerophosphate-induced osteoblastic differentiation," J Cell Biochem 112, Jun. 22, 2010, pp. 71-77.

Nieder et al., "Pathologic fracture and metastatic spinal cord compression in patients with prostate cancer and bone metastases," BMC Urol10:23, Dec. 22, 2010, 7 pages.

Ortlund et al., "Crystal Structures of Human Prostatic Acid Phosphatase in Complex with a Phosphate Ion and α-Benzylaminobenzylphosphonic Acid Update the Mechanistic Picture and Offer New Insights into Inhibitor Design," Biochemistry 2003, Dec. 21, 2002, 42, pp. 383-389.

Pinkas-Kramarski et al., "The oncogenic ErbB-2/ErbB-3 heterodimer is a surrogate receptor of the epidermal growth factor and beta cellulin," Oncogene 16, Oct. 13, 1997, pp. 1249-1258.

Roudier MP et al., "Histopathological assessment of prostate cancer bone osteoblastic metastases," J Urol., Sep. 2008, 180(3), pp. 1154-1160.

Roudier MP et al., "Phenotypic Heterogeneity of End-Stage Prostate Carcinoma Metastatic to Bone," Hum Pathol., Feb. 20, 2003, 34, pp. 646-653.

Schneider et al., "High cortical bone mass phenotype in betacellulin transgenic mice is EGFR dependent,"Dec. 1, 2008, J Bone Miner Res 24(3), pp. 455-467.

Seitz et al., "Retinol deprivation partially rescues the skeletal mineralization defects of Phex-deficient Hyp mice," Bone 53, Dec. 12, 2012, pp. 231-238.

Sheu et al., "A phage display technique identifies a novel regulator of cell differentiation," J Bio Chem 278, Jan. 2003, pp. 438-443.

Sturge et al., "Bone metastasis in prostate cancer: emerging therapeutic strategies," Aug. 5, 2011, Nat Rev Clin Oncol 8, pp. 357-368.

Thudi et al.,"Dickkopf-1 (OKK-1) stimulated prostate cancer growth and metastasis and inhibited bone formation in osteoblastic bone metastases," Prostate 71, Oct. 18, 2010, pp. 615-625.

Valkenburg, et al. "Skeletal metastasis: treatments, mouse models, and the Wnt signaling" Chinese Journal of Cancer, 2013 32(7), pp. 380-396.

Vovk et al., "Stereoselectivity of binding of alpha-(Nbenzylamino) benzylphosphonic adds to prostatic acid phosphatase," Bioorg Med Chem let 18, Jul. 2008, pp. 4620-4623.

Wittrant et al., "RANKL/RANK/OPG: new therapeutic targets in bone tumours and associated osteolysis," Biochim Biophys Acta 1704, Jun. 17, 2004, pp. 49-57.

Yoshiko et al., "Stanniocalcin 1 stimulates osteoblast differentiation in rat calvaria cell cultures," Endocrinology 144(9), Sep. 2003, pp. 4134-4143.

Zhang et al., "Androgen receptor variants occur frequently in castration resistant prostate cancer metastases," PLoS One 6:e27970, Nov. 17, 2011, 11 pages.

* cited by examiner

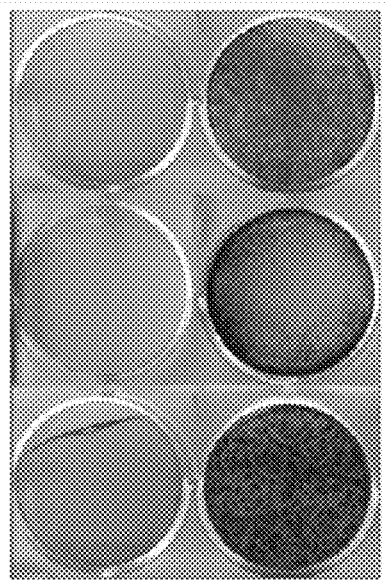
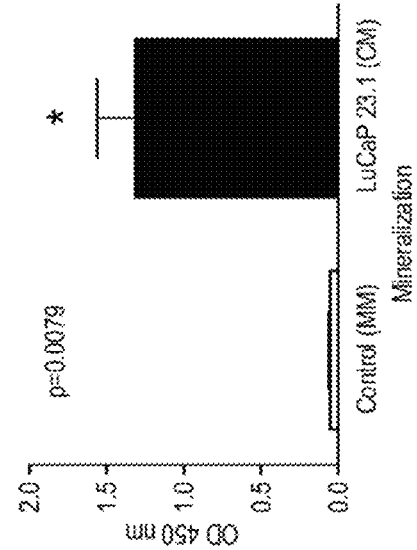
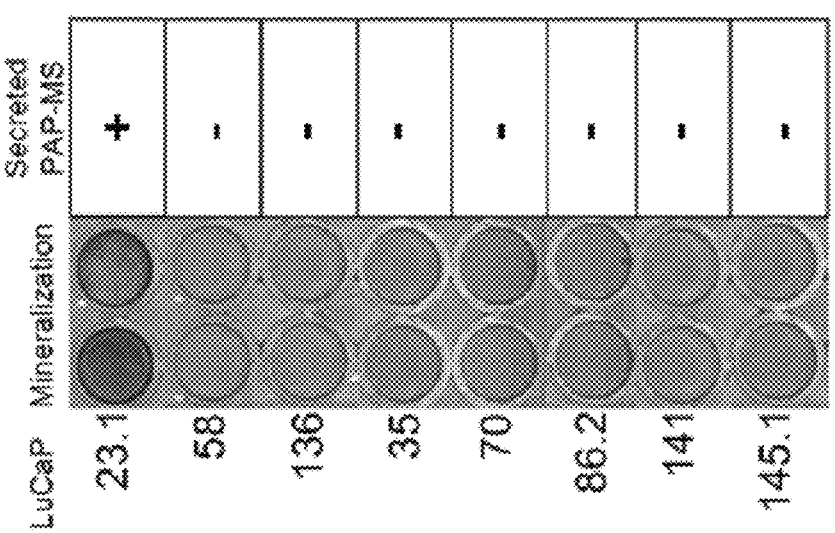
FIG. 2B
FIG. 2C
FIG. 2A

METHODS FOR TREATING AND PREVENTING PROSTATE CANCER BONE METASTASES

CROSS-REFERENCE TO RELATED APPLICATIONS

This application claims the benefit of U.S. Provisional Application No. 62/079,698, filed Nov. 14, 2014, which is hereby incorporated by reference in its entirety.

STATEMENT REGARDING FEDERALLY SPONSORED RESEARCH

This invention was made with government support under Grant No. P50CA97186, awarded by the National Institutes of Health (NIH). The government has certain rights in the invention.

TECHNICAL FIELD

The present disclosure relates generally to methods of treating a subject having a prostate cancer bone metastasis. The present disclosure also relates to methods of prophylactically treating a subject at risk of developing a prostate cancer bone metastasis. In particular, the methods may comprise administering an inhibitor of prostatic acid phosphatase to the subject. More particularly, the methods may comprise administering a phosphonic acid to the subject.

BACKGROUND

Prostate cancer (PCa) can preferentially metastasize to the bone, with bone involvement occurring in 90% of patients with metastatic disease. These metastases can cause severe bone pain, replacement of bone marrow, pathologic fracture, and spinal cord compression (see Bubendorf L, et al. (2000) Hum Pathol 31:578-583 and Nieder C, et al. (2010) BMC Urol 10:23). The evaluation of bone metastases obtained through studies of rapid autopsies have shown that bone turnover can increase in these metastatic sites; however, the new bone can form layers of fragile, woven bone with reduced mechanical strength (see Roudier M P, et al. (2008) J Urol 180:1154-1160; Jin J K, et al. (2011) Int J Cancer 128:2545-2561; and Morrissey C, et al. (2013) J Bone Miner Res 28:333-340). In concert with the heterogeneity of bone formation, there can be a wide spectrum of responses to treatment. A number of therapies have been developed to address osteolytic bone metastases, such as bisphosphonates (e.g., zoledronic acid), and more recently, RANKL inhibitors (e.g., Denosumab) (see Fizazi K, et al. (2011) Lancet 377:813-822; Lee R J, et al. (2011) Bone 48:88-95; Valkenburg K C, et al. (2013) Chin J Cancer 32:380-396; and Sturge J, et al. (2011) Nat Rev Clin Oncol 8:357-368). Additionally, a number of factors have been described as possible targets to treat osteoblastic bone metastases including, but not limited to, ET-1, Wnt signaling proteins, and the TGF-β superfamily, including the BMPs (see Valkenburg K C, et al. (2013) Chin J Cancer 32:380-396; Sturge J, et al. (2011) Nat Rev Clin Oncol 8:357-368; Bagnato A, et al. (2011) Br J Pharmacol 163:220-233; Larson S R, et al. (2013) Prostate 73:932-940; and Feeley B T, et al. (2005) J Bone Miner Res 20:2189-2199). While these proteins can promote bone formation in vitro, the specific mechanisms that promote bone growth in PCa patients are largely unknown. Therefore, there has been focus on targeting soluble proteins secreted from tumor cells that promote bone growth within the bone-tumor microenvironment.

One of the major proteins secreted by normal prostatic epithelium and PCa tumor cells is prostatic acid phosphatase (PAP). In 1936, Gutman, et al. described an increase of phosphatase activity at osteoblastic skeletal metastatic sites, indicating that the production of phosphatases may play an important role in dictating the osteoblastic behavior of bone metastasis (see Gutman E B, et al. (1936) Am J Cancer 28:485-495). It was subsequently described that PAP, when added to cell culture, can stimulate collagen synthesis and alkaline phosphatase production in osteoprogenitor cells and osteoblasts. This led to the hypothesis that PAP may directly stimulate bone forming cells, likely contributing to the sclerotic pattern at sites of PCa bone metastases (see Ishibe M, et al. (1991) J Clin Endocrinol Metab 73:785-792). More recently, it was shown that secreted PAP can be expressed in clinical osteosclerotic PCa bone metastases themselves, and that PAP may play a causal role in the osteoblastic nature of PCa bone metastases (see Kirschenbaum A, et al. (2011) Ann N Y Acad Sci 1237:64-70).

BRIEF DESCRIPTION OF THE DRAWINGS

The embodiments disclosed herein will become more fully apparent from the following description and appended claims, taken in conjunction with the accompanying drawings.

FIG. 2A depicts the results of Alizarin Red experiments illustrating that only the osteoblastic PCa xenografts, LuCaP 23.1, promoted mineralization in MC3T3-E1 mouse osteoblast-like cells. Also depicted are mass spectrometry (MS) results indicating that only LuCaP 23.1 secreted sufficient detectable prostatic acid phosphatase (PAP).

FIG. 2B depicts the results of Alizarin Red staining showing that LuCaP 23.1 conditioned media (CM) promoted mineralization in HCO cells (human calvarial osteoblasts).

FIG. 2C is a graph depicting that LuCaP 23.1 conditioned media (CM) significantly promoted mineralization in HCO cells in comparison to HCO cells cultured in the presence of mineralization media (MM) (* p=0.0079).

DETAILED DESCRIPTION

Figure 1A:
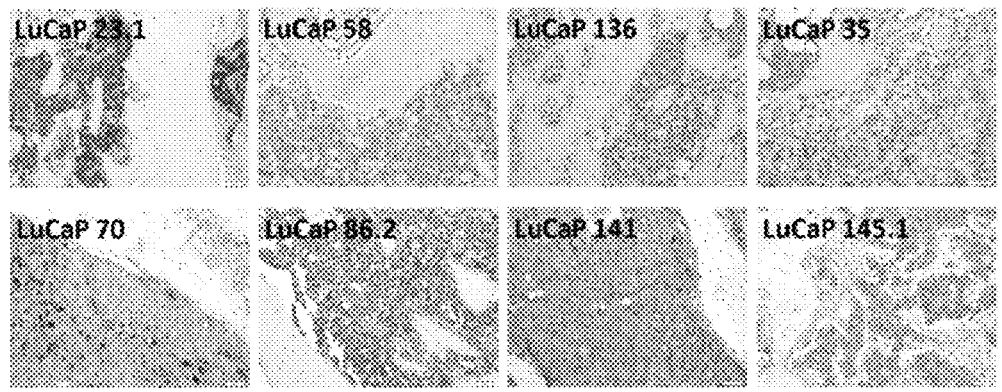
FIG. 1A is a series of images of the prostate cancer (PCa) xenograft lines, LuCaP 23.1, LuCaP 58, LuCaP 136, LuCaP 35, LuCaP 70, LuCaP 86.2, LuCaP141, and LuCaP 145.1, showing intratibial prostatic acid phosphatase (PAP) staining.

The present disclosure relates generally to methods for treating a subject having a prostate cancer (PCa) bone metastasis. The present disclosure also relates to methods for prophylactically treating a subject at risk of developing a PCa bone metastasis. The methods for treating a subject having, or at risk of developing, a PCa bone metastasis may comprise administering to the subject a phosphonic acid (PA); a biologically active derivative of a PA; or a pharmaceutically acceptable salt, ester, solvate, isomer or complex of a PA. Further, the methods for treating a subject having, or at risk of developing, a PCa bone metastasis may comprise administering a benzylaminophosphonic acid (e.g., [phenyl[(phenylmethyl)amino]methyl]-phosphonic acid) to the subject. The methods for treating a subject having, or at risk of developing, a PCa bone metastasis may also comprise administering a prostatic acid phosphatase (PAP) inhibiting agent to the subject.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

Treating a subject can comprise delivering an effective amount or delivering a prophylactic treatment and/or a therapeutic treatment to a subject (e.g., a patient). As used herein, an "effective amount" is an amount of a compound that can result in a desired physiological change in a subject. Effective amounts may also be administered for research purposes.

As used herein, a "prophylactic treatment" or a "method of prophylactically treating" comprises a treatment administered to a subject who does not display signs or symptoms of a disease or condition, or a subject who displays only early signs or symptoms of a disease or condition, such that treatment is administered for the purpose of diminishing, preventing, and/or decreasing the risk of further developing the disease or condition or of diminishing, preventing, and/or decreasing the risk of developing the disease or condition. Thus, a prophylactic treatment may function as a preventative treatment against a disease or condition.

As used herein, a "therapeutic treatment" comprises a treatment administered to a subject who displays symptoms or signs of a disease or a condition and the therapeutic treatment is administered to the subject for the purpose of diminishing or eliminating the symptoms or the signs of the disease or the condition.

As used herein, "therapeutically effective amounts" comprise amounts that provide prophylactic treatment and/or therapeutic treatment. Therapeutically effective amounts need not fully prevent or cure the disease or the condition but can also provide a partial benefit, such as a delay of onset or an alleviation or an improvement of at least one symptom of the disease or the condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes the $IC_{50}$ as determined in cell culture. Such information can be used to more accurately determine useful doses in subjects of interest.

The actual dose amount administered to a particular subject can be determined by a physician, a veterinarian, or a researcher, taking into account parameters such as, but not limited to, physical and physiological factors including body weight, severity of condition, type of disease, previous or concurrent therapeutic interventions, idiopathy of the subject, and/or route of administration.

Doses can range from 0.1 mg/kg/day to 5 mg/kg/day, or from 0.5 mg/kg/day to 1 mg/kg/day, or from 0.1 mg/kg/day to 5 µg/kg/day, or from 0.5 mg/kg/day to 1 µg/kg/day. In other non-limiting examples, a dose can comprise 1 µg/kg/day, 5 µg/kg/day, 10 µg/kg/day, 50 µg/kg/day, 100 µg/kg/day, 200 µg/kg/day, 350 µg/kg/day, 500 µg/kg/day, 1 mg/kg/day, 5 mg/kg/day, 10 mg/kg/day, 50 mg/kg/day, 100 mg/kg/day, 200 mg/kg/day, 350 mg/kg/day, 500 mg/kg/day, or 1000 mg/kg/day. Therapeutically effective amounts can be achieved by administering single or multiple doses during the course of a treatment regimen (i.e., days, weeks, months, etc.).

Pharmaceutically acceptable salts, tautomers, and isomers of the compounds disclosed herein can also be used. Exemplary salts can include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The formulations described herein can be administered by, without limitation, injection, inhalation, infusion, perfusion, lavage, and/or ingestion. Routes of administration can include, but are not limited to, intravenous, intradermal, intraarterial, intraperitoneal, intralesional, intracranial, intraarticular, intraprostatic, intrapleural, intratracheal, intranasal, intravitreal, intravaginal, intrarectal, topical, intratumoral, intramuscular, intravesicular, intrapericardial, intraumbilical, intraoculatal, mucosal, oral, subcutaneous, and/or subconjunctival.

In some embodiments, for injection, formulations can be made as aqueous solutions, such as in buffers including, but not limited to, Hanks' solution, Ringer's solution, and/or physiological saline. The solutions can contain formulatory agents such as suspending, stabilizing, and/or dispersing agents. Alternatively, the formulation can be in lyophilized and/or powder form for constitution with a suitable vehicle control (e.g., sterile pyrogen-free water) before use.

Any formulation disclosed herein can advantageously comprise any other pharmaceutically acceptable carrier or carriers, which comprise those that do not produce significantly adverse, allergic, or other untoward reactions that may outweigh the benefit of administration, whether for research, prophylactic, and/or therapeutic treatments. Exemplary pharmaceutically acceptable carriers and formulations are disclosed in Remington's Pharmaceutical Sciences, 18th Ed., Mack Printing Company, 1990, which is incorporated by reference herein for its teachings regarding the same. Moreover, formulations can be prepared to meet sterility, pyrogenicity, general safety, and purity standards as required by the United States FDA's Division of Biological Standards and Quality Control and/or other relevant U.S. and foreign regulatory agencies.

Exemplary, generally used pharmaceutically acceptable carriers may comprise, but are not limited to, bulking agents or fillers, solvents or co-solvents, dispersion media, coatings, surfactants, antioxidants (e.g., ascorbic acid, methionine, and vitamin E), preservatives, isotonic agents, absorption delaying agents, salts, stabilizers, buffering agents, chelating agents (e.g., EDTA), gels, binders, disintegration agents, and/or lubricants.

Exemplary buffering agents may comprise, but are not limited to, citrate buffers, succinate buffers, tartrate buffers, fumarate buffers, gluconate buffers, oxalate buffers, lactate buffers, acetate buffers, phosphate buffers, histidine buffers, and/or trimethylamine salts.

Exemplary preservatives may comprise, but are not limited to, phenol, benzyl alcohol, meta-cresol, methylparaben, propyl paraben, octadecyldimethylbenzyl ammonium chloride, benzalkonium halides, hexamethonium chloride, alkyl parabens (such as methyl or propyl paraben), catechol, resorcinol, cyclohexanol, and/or 3-pentanol.

Exemplary isotonic agents may comprise polyhydric sugar alcohols comprising, but not limited to, trihydric or higher sugar alcohols, (e.g., glycerin, erythritol, arabitol, xylitol, sorbitol, and/or mannitol).

Exemplary stabilizers may comprise, but are not limited to, organic sugars, polyhydric sugar alcohols, polyethylene glycol, sulfur-containing reducing agents, amino acids, low molecular weight polypeptides, proteins, immunoglobulins, hydrophilic polymers, and/or polysaccharides.

Formulations can also be depot preparations. In some embodiments, such long-acting formulations may be administered by, without limitation, implantation (e.g., subcutaneously or intramuscularly) or by intramuscular injection. Thus, for example, compounds can be formulated with suitable polymeric and/or hydrophobic materials (e.g., as an emulsion in an acceptable oil) or ion exchange resins, or as sparingly soluble derivatives (e.g., as a sparingly soluble salt).

Additionally, in various embodiments, compounds can be delivered using sustained-release systems, such as semipermeable matrices of solid polymers comprising at least one compound. Various sustained-release materials have been established and are well known by those of ordinary skill in the art. Sustained-release capsules may, depending on their chemical nature, release the compound following administration for a few weeks up to over 100 days.

A first aspect of the disclosure relates to methods for treating, or methods for therapeutic treatment of, a subject or a patient having one or more prostate cancer (PCa) bone metastases.

In some embodiments, this disclosure provides methods of treating a subject having one or more PCa bone metastases comprising administering to the subject a therapeutically effective amount of a pharmaceutical composition. In certain embodiments, the pharmaceutical composition may be an inhibitor of prostatic acid phosphatase (PAP). In various embodiments, the pharmaceutical composition may comprise a phosphonic acid (PA); a biologically active derivative of a PA; and/or a pharmaceutically acceptable salt, ester, solvate, isomer, and/or complex of a PA and/or a biologically active derivative of a PA. The therapeutically effective amount of the pharmaceutical composition may also comprise a pharmaceutically acceptable carrier.

In certain embodiments, methods for treating a subject having one or more PCa bone metastases may further comprise identifying a subject having one or more PCa bone metastases. For example, a practitioner may identify a subject having at least one PCa bone metastasis and the practitioner may then administer a therapeutically effective amount of the pharmaceutical composition to the subject. The subject may be a human, a mammal, or another suitable subject.

In various embodiments, the PA may be a benzylaminophosphonic acid; a biologically active derivative of a benzylaminophosphonic acid; and/or a pharmaceutically acceptable salt, ester, solvate, isomer, and/or complex of a benzylaminophosphonic acid and/or a biologically active derivative of a benzylaminophosphonic acid. In some embodiments, the PA may be [phenyl[(phenylmethyl)amino]methyl]-phosphonic acid (CAS Registry Number 25881-35-0).

In certain embodiments, the pharmaceutical composition may reduce or be configured to reduce a pathological effect or symptom of the PCa bone metastasis. The pathological effect or symptom of the PCa bone metastasis may be selected from, but not limited to, at least one of bone pain, one or more bone fractures, spinal cord compression, and/or an increased blood calcium level. In various embodiments, the subject may have at least one of, but not limited to, a stage III PCa, a stage IV PCa, a late-stage PCa, an end-stage PCa, and/or a castration-resistant PCa.

Another aspect of the disclosure relates to methods of prophylactically treating, or methods for prophylactic treatment of, a subject or patient at risk of developing one or more PCa bone metastases.

In some embodiments, the disclosure provides methods of prophylactically treating a subject at risk of developing one or more PCa bone metastases comprising administering to the subject a therapeutically effective amount of a pharmaceutical composition. In certain embodiments, the pharmaceutical composition may be an inhibitor of PAP. In various embodiments, the pharmaceutical composition may comprise a PA; a biologically active derivative of a PA; and/or a pharmaceutically acceptable salt, ester, solvate, isomer, and/or complex of a PA and/or a biologically active derivative of a PA. The therapeutically effective amount of the pharmaceutical composition may also comprise a pharmaceutically acceptable carrier.

In certain embodiments, methods for prophylactically treating a subject at risk of developing one or more PCa bone metastases may further comprise identifying a subject having PCa. Methods for prophylactically treating a subject at risk of developing one or more PCa bone metastases may also comprise identifying a subject at risk of developing one or more PCa bone metastases. For example, a practitioner may identify a subject at risk of developing one or more PCa bone metastases and then the practitioner may administer a therapeutically effective amount of the pharmaceutical composition to the subject. The subject may be a human, a mammal, or another suitable subject.

In various embodiments, the PA may be a benzylaminophosphonic acid; a biologically active derivative of a benzylaminophosphonic acid; and/or a pharmaceutically acceptable salt, ester, solvate, isomer, and/or complex of a benzylaminophosphonic acid and/or a biologically active derivative of a benzylaminophosphonic acid. In some embodiments, the PA may be [phenyl[(phenylmethyl)amino]methyl]-phosphonic acid (CAS Registry Number 25881-35-0).

In certain embodiments, the pharmaceutical composition may reduce or be configured to reduce a risk of developing one or more PCa bone metastases. The pharmaceutical composition may also reduce or be configured to reduce a risk of developing a pathological effect or symptom associated with a PCa bone metastasis. The pathological effect or symptom associated with the PCa bone metastasis may be selected from at least one of, but not limited to, bone pain, one or more bone fractures, spinal cord compression, and/or an increased blood calcium level. In various embodiments, the subject may have at least one of, but not limited to, a stage III PCa, a stage IV PCa, a late-stage PCa, an end-stage PCa, and/or a castration-resistant PCa.

Another aspect of the disclosure relates to methods for treating, or methods for therapeutic treatment of, a pathological effect or symptom of one or more PCa bone metastases in a subject or a patient.

In some embodiments, this disclosure provides methods for treating a pathological effect or symptom of a PCa bone metastasis in a subject comprising administering to the subject a therapeutically effective amount of a pharmaceutical composition. In various embodiments, the pharmaceutical composition may comprise a PAP inhibiting agent.

In certain embodiments, the PAP inhibiting agent may be selected from a PA; a biologically active derivative of a PA; and/or a pharmaceutically acceptable salt, ester, solvate, isomer, and/or a complex of a PA and/or a biologically active derivative of a PA. In some embodiments, the PAP inhibiting agent may selected from a benzylaminophosphonic acid; a biologically active derivative of a benzylaminophosphonic acid; and/or a pharmaceutically acceptable salt, ester, solvate, isomer, and/or a complex of a benzylaminophosphonic acid and/or a biologically active derivative of a benzylaminophosphonic acid. In various embodiments, the PAP inhibiting agent may be a [phenyl[(phenylmethyl)amino]methyl]-phosphonic acid (CAS Registry Number 25881-35-0).

In some embodiments, the pathological effect or symptom of the one or more PCa bone metastases may be selected from at least one of, but not limited to, bone pain, one or more bone fractures, spinal cord compression, and/or an increased blood calcium level. Methods for treating a pathological effect or symptom of a PCa bone metastasis in a subject may further comprise identifying a subject having a pathological effect or symptom of a PCa bone metastasis. In some embodiments, the subject may have at least one of, but not limited to, a stage III PCa, a stage IV PCa, a late-stage PCa, an end-stage PCa, and/or a castration-resistant PCa. In certain embodiments, the subject may have at least one of, but not limited to, bone pain, one or more bone fractures, spinal cord compression, and/or an increased blood calcium level. Furthermore, the subject may be a human, a mammal, or another suitable subject.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Preparation and Characterization of LuCaP PCa Xenografts

Minimum Essential Medium (MEM) was conditioned for 48 hours with 0.05 g/ml minced LuCaP tumor tissue from eight different LuCaP PCa xenograft lines (LuCaP 23.1, 35, 58, 70, 86.2, 136, 141, and 145.1), supplemented with 10% fetal bovine serum (FBS), 10 mM β-glycerol phosphate in Hank's balanced salt solution (HBSS), and 50 µg/ml L-ascorbic acid. CM was centrifuged for 10 minutes at 16,000 relative centrifugal force (RCF), filtered through a 2 µm filter and used for mass spectrometry. In addition, to determine which CM promoted mineralization in vitro, 2 ml of CM was added to wells containing MC3T3-E1 cells (an osteoblastic precursor cell line derived from mouse calvaria), seeded in a six-well plate at 100,000 cells per well, and allowed to come to confluence. Control wells of each plate were treated with MM (10% FBS in MEM with 10 mM β-glycerol phosphate in HBSS (SIGMA-ALDRICH®, St. Louis, Mo.), and 50 µg/ml L-ascorbic acid). Mineralization was determined by Alizarin Red assay as described below.

Example 2—Mass Spectometry

CM was used for mass spectrometry. The proteins from the CM were precipitated, alkylated, and after tryptic digestion, the peptide mixture was desalted using a SEP-PAK® C18 cartridge. The eluent was fractionated by a SCX™ column into ten fractions. The fractions were concentrated, and reconstituted in 10 µl of 5% formic acid for LC-MS/MS analysis.

High-performance liquid chromatography (HPLC): CAPLC™ (WATERS®, USA) Column: VYDAC® C18 (5 µm ID×150 mm, VYDAC®, CA) Trapping column: VYDAC® C18 EV 300 A, 10 µm Solvent A: 5% $CH_3CN$+ 0.1% formic acid+0.01% TFA Solvent B: 85% $CH_3CN$+ 10% isopropanol+5% $H_2O$+0.1% formic acid+0.01% TFA Flow rate: 250 nl/min Gradient: 100 min linear gradient from 10% to 100% B MS/MS: Q-TOF2 (MICROMASS®/WATERS®, USA). Peak list was created using MASCOT DISTILLER™ 2.3 software from MATRIX SCIENCE™ with a processing macro that smoothes, centroids, and assesses the quality of data. In-house MASCOT™ 2.3 from MATRIX SCIENCE™ (London, UK) was used to assist the interpretation of tandem mass spectra against the IPI mouse database. Variable modifications including deamidation (N, Q), oxidation (M), and carbamidomethylation (C) were considered for the searching.

Example 3—Alizarin Red Mineralization Assays

Cultured cells, HCO or MC3T3-E1, were seeded at 50,000 cells/well in MEM and 10% FBS. MM was added to all cultures 1-2 days after seeding and replaced every other day. MM, LuCaP 23.1 CM (5%, 10%, or 20%), PAP, lyophilized powder obtained from human prostatic fluid (CSI 14633A; CELL SCIENCES®, Canton, Mass.) or phosphonic acid, P-[phenyl[(phenylmethyl)amino]methyl]- (CAS#25881-35-0; AURORA FINE CHEMICALS™ LLC, San Diego, Calif.) was added to cultures typically on day 5-6, before mineralization occurred. After mineralization, cells were fixed in 10% formalin for 20 minutes and then washed. 2% Alizarin Red was added to air-dried plates. After washing, retained dye was extracted in a solution of 20% methanol and 10% acetic acid in water, and absorbance was measured at 405 nm.

Example 4—Tissue Acquisition and Processing

Human PCa metastases were obtained as part of the University of Washington Medical Center PCa Donor Rapid Autopsy Program, which is approved by the University of Washington Institutional Review Board (see Roudier M P, et al. (2003) Hum Pathol 34:646-653). To assess PAP expression in PCa metastases, a tissue microarray consisting of 160 metastatic sites from 50 patients (83 bone metastases and 77 soft tissue metastases) was stained. To compare PAP expression in highly osteoblastic and osteolytic PCa bone metastases, thirty-three bone samples from rapid autopsies of 30 patients who died with a diagnosis of metastatic CRPC were processed. From 30 patients (n=33), metastatic cores were isolated at autopsy and divided into two portions—one flash frozen in liquid nitrogen to be used for RNA isolation and one decalcified in formic acid, fixed in 10% neutral buffered formalin, and embedded in paraffin used for IHC. From a selected subset of 11 patients, seven bone metastases were identified as highly osteoblastic and seven as highly osteolytic. The corresponding frozen tissue was used for RNA isolation. Macroscopic assessment of paraffin embedded tissues from the same bone cores confirmed specimens to be at least 90% tumor (clinical data associated with these samples can be found in Larson S R, et al. (2013) Prostate 73:932-940). LuCaP xenograft tumored tibae were processed in similar fashion to the patient metastatic bone cores.

Example 5—RNA Amplification and Microarray Hybridization

To determine the effect of LuCaP 23.1 CM on mineralization, BMSC isolated from normal bone marrow aspirates of three patients were seeded at 100,000 cells/well, allowed to come to confluence, and then treated with MM (MM was replaced every third day). Cultures were then treated with LuCaP 23.1 CM for 48 hours or with MM alone. Total RNA was extracted using STAT-60™ (TEL-TEST™, Inc. Friendswood, Tex.) according to the manufacturer's protocol. A reference standard RNA for use in two-color oligo arrays was prepared and total RNA from BMSC as well as reference total RNA samples were amplified and hybridized to AGILENT™ 44K whole human genome expression oligonucleotide microarray slides (see Larson S R, et al. (2013) Prostate 73:932-940). The Statistical Analysis of Microarray (SAM) program was used to analyze expression differences between CM and MM groups using unpaired, two-sample t-tests on all probes passing filters and controlled for multiple testing by estimation of q-values using the false discovery rate (FDR) method (see Zhang X, et al. (2011) PLoS One 6:e27970). Microarray data were deposited in the Gene Expression Omnibus (GEO) database under the accession number GSE48907. To compare to profiles of human osteoblastic and osteolytic bone metastases, an expression dataset containing 14 bone metastases previously published under the GEO accession GSE41619 was used (see Larson S R, et al. (2013) Prostate 73:932-940).

Example 6—Quantitative Reverse Transcription-Polymerase Chain Reaction (qRT-PCR)

Primers (INTEGRATED DNA TECHNOLOGIES®, Coralville, Iowa), which are listed in Table 1 below, were designed to span intron-exon boundaries using Primer3 software (http://frodo_wi_mit_edu). One microgram of either amplified or total RNA from each sample was reverse transcribed into cDNA using the ADVANTAGE® RT-FOR-PCR KIT for random hexamer priming according to manufacturer's protocol (BD BIOSCIENCES™, Palo Alto, Calif.). Reactions contained 10 µl of ABSOLUTE QPCR SYBR GREEN MIX™ (THERMO SCIENTIFIC™, Wilmington, Del.), 2 µl of cDNA template (1:10 dilution of reverse transcribed RNA), 0.4 µl each of forward and reverse primer (200 nM), and 7.2 µl $H_2O$. qRT-PCR was performed on a ROTOR-GENE RG-3000® (CORBETT RESEARCH™, Sydney, Australia) using the following parameters: 95° C. for 15 minutes followed by 40 cycles of denaturing at 95° C. for 15 seconds and annealing/extension at T(m)/72° C. for 30 seconds each. qRT-PCR quality was accessed using a four-fold dilution standard curve of LuCaP 23.1 cDNA with a $R^2$ value >0.99. Amplicon product was confirmed by melt curve analysis and gel electrophoresis. Using cycle threshold values, average expression levels were normalized against β-actin. Fold changes and significance using paired t-tests were determined between experimental groups.

| Gene | Forward Sequence | Reverse Sequence | Tm |
|------|------------------|------------------|-----|
| ACPP | 5'-tctaggctccaaggggtgtc-3'<br>(SEQ ID NO: 1) | 5'-gtgctgcgtctcattccgatag-3'<br>(SEQ ID NO: 2) | 56° C. |
| ACTB | 5'-gcactcttccagccttccttcct-3'<br>(SEQ ID NO: 3) | 5'-actcgtcatactcctgcttgctga-3'<br>(SEQ ID NO: 4) | 69° C. |
| ASPN | 5'-ttagcccttcacacatcgcactga-3'<br>(SEQ ID NO: 5) | 5'-atggaatgttggttgggactgagg-3'<br>(SEQ ID NO: 6) | 69° C. |
| BMP2 | 5'-aggaggcaaagaaaaggaacggac-3'<br>(SEQ ID NO: 7) | 5'-gggaagcagcaacgctagaagac-3'<br>(SEQ ID NO: 8) | 56° C. |
| BTC | 5'-ccaccacacaatcaaagcggaaag-3'<br>(SEQ ID NO: 9) | 5'-tcaactctctcacaccttgctcca-3'<br>(SEQ ID NO: 10) | 58° C. |
| CCL20 | 5'-ggcgaatcagaagcagcaagcaac-3'<br>(SEQ ID NO: 11) | 5'-agtgaaacctccaaccccagcaag-3'<br>(SEQ ID NO: 12) | 69° C. |
| EGFR | 5'-tgctggatgatagacgcagatagt-3'<br>(SEQ ID NO: 13) | 5'-cagggcacggtagaagttggag-3'<br>(SEQ ID NO: 14) | 54° C. |
| ENPP1 | 5'-tctttgttggctatggacctggatt-3'<br>(SEQ ID NO: 15) | 5'-ttatctctggggtttcttgtgaagg-3'<br>(SEQ ID NO: 16) | 69° C. |
| EPHA4 | 5'-cccaagccccataaccctaact-3'<br>(SEQ ID NO: 17) | 5'-tttcatcagtgtctttgcccagaa-3'<br>(SEQ ID NO: 18) | 69° C. |
| HIF1A | 5'-caccactaccactgccaccact-3'<br>(SEQ ID NO: 19) | 5'-catgttccatttttcgctttctctg-3'<br>(SEQ ID NO: 20) | 54° C. |
| OSR2 | 5'-tctgacgaagacgtggatctgct-3'<br>(SEQ ID NO: 21) | 5'-ctccgacaaaaacccagtgagac-3'<br>(SEQ ID NO: 22) | 67° C. |
| PDPN | 5'-tgactccaggaaccagcgaag-3'<br>(SEQ ID NO: 23) | 5'-gcgaatgcctgttacactgttga-3'<br>(SEQ ID NO: 24) | 69° C. |
| PHEX | 5'-gtgccctcccttatgttgttgga-3'<br>(SEQ ID NO: 25) | 5'-ttggctttccttttcgttcctgca-3'<br>(SEQ ID NO: 26) | 69° C. |
| PTN | 5'-cacaatgccgaatgccagaagac-3'<br>(SEQ ID NO: 27) | 5'-tgctgatgtccttttatgttccac-3'<br>(SEQ ID NO: 28) | 69° C. |
| SDC1 | 5'-tgaccttcacactccccacacag-3'<br>(SEQ ID NO: 29) | 5'-gctgccttcgtccttcttcttcat-3'<br>(SEQ ID NO: 30) | 69° C. |
| SPP1 | 5'-ccagcaaccgaagttttcactcca-3'<br>(SEQ ID NO: 31) | 5'-tgcaccattcaactcctcgctttc-3'<br>(SEQ ID NO: 32) | 69° C. |
| STC1 | 5'-tttccaaaggatgattgctgaggtg-3'<br>(SEQ ID NO: 33) | 5'-ctgtctctgattgtgctgactgtg-3'<br>(SEQ ID NO: 34) | 69° C. |
| TGM2 | 5'-ccagggtgacaagagcgagatga-3'<br>(SEQ ID NO: 35) | 5'-tccttgatggcacgaactggaact-3'<br>(SEQ ID NO: 36) | 69° C. |
| VEGFA | 5'-atggcagaaggaggagggcagaa-3'<br>(SEQ ID NO: 37) | 5'-caggggcacacaggatggcttg-3'<br>(SEQ ID NO: 38) | 69° C. |
| VEGFB | 5'-gacatcacccatcccactccag-3'<br>(SEQ ID NO: 39) | 5'-ggctcctctttgttcccccact-3'<br>(SEQ ID NO: 40) | 54° C. |

Example 7—Immunohistochemistry

Formalin-fixed paraffin-embedded tissue sections (5 μm) were deparaffinized and rehydrated. Antigen retrieval was performed with 10 mM citrate buffer (pH 6.0) in a pressure cooker (20 psi for 5 minutes) as needed. Endogenous peroxide was quenched by 3% $H_2O_2$ for 15 minutes and avidin/biotin were blocked respectively with corresponding reagents (VECTOR LABORATORIES™, Inc.). After incubation with 5% normal goat-horse-chicken serum at room temperature for 1 hour, primary antibodies, PAP (AB-CAM®, Ab75704), or BTC (R&D SYSTEMS®, Inc, ANU02) were added at 4° C. overnight followed by biotinylated secondary antibody (1:150) (VECTOR LABORATORIES™, Inc.) and ABC reagent (VECTOR LABORATORIES™, Inc.), 30 minutes each. DAB (INVITROGEN™) was used as chromogen. All sections were counterstained with hematoxylin and mounted with CYTOSEAL™ XYL (RICHARD-ALLAN SCIENTIFIC™). Mouse or goat IgG was used at the same concentration as the primary antibody for negative controls.

Example 8—Immunohistochemical Assessment and Analysis

Immunostaining was assessed using a quasi-continuous score system, created by multiplying each intensity level ("0" for no brown color, "1" for faint and fine brown chromogen deposition, and "2" for clear and coarse granular chromogen clumps) with the corresponding percentage of cells expressing the particular intensity, and then summing all values to a final score for each sample (scores ranging from 0-200) (see Zhang X, et al. (2011) PLoS One 6:e27970). The distribution of the final scores were grouped as "none" (score range: 0), "weak" (score range: 0~100), "moderate" (score range: 100~150), and "intense" (score range: 150~200). Missing or damaged sections were excluded from analysis. Significance of differences were calculated using a paired t-test, with p values ≤0.05 indicating statistical significance.

Figure 1B:
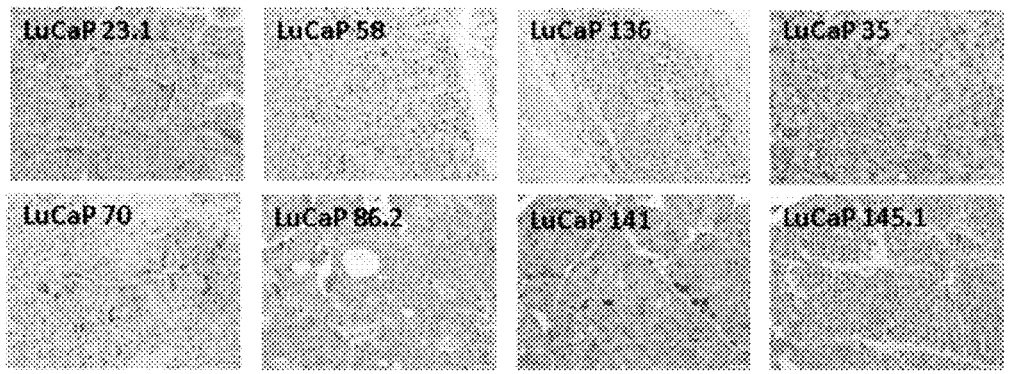
FIG. 1B is a series of images of the PCa xenograft lines of FIG. 1A showing subcutaneous PAP staining.
Figure 1C:
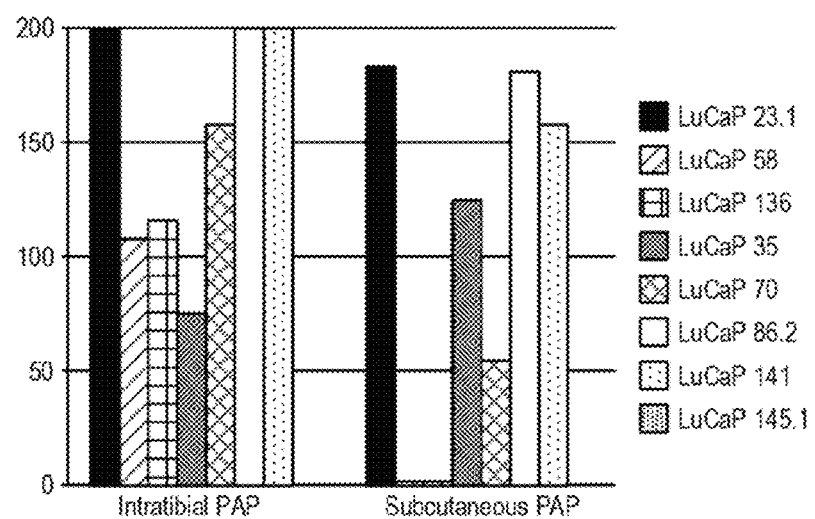
FIG. 1C is a graph depicting intratibial PAP and subcutaneous PAP expression in the PCa xenograft lines of FIG. 1A, as indicated.

Example 9—LuCaP 23.1 Prostate Carcinoma CM Induces Mineralization and Comprises PAP The PCa xenograft lines, LuCaP 23.1, LuCaP 58, and LuCaP 136, elicit osteoblastic reactions in murine tibiae. LuCaP 35 displays a mixed bone response and LuCaP 70, LuCaP 86.2, LuCaP 141, and LuCaP 145.1 are osteolytic. When evaluating PAP expression in LuCaP models in the bone environment (intra-tibial), LuCaP 23.1, LuCaP 70, LuCaP 86.2, and LuCaP 141 displayed intense PAP staining; LuCaP 58 and LuCaP 136 exhibited moderate staining. Only LuCaP 35 and LuCaP 145.1 intra-tibial tumors had weak to no expression (see FIGS. 1A-1C). Because the microenvironment can influence gene expression, subcutaneous LuCaP tumors were also stained for PAP (see FIGS. 1A-1C). LuCaP 23.1 exhibited strong immunoreactivity, however, the two other osteoblastic xenograft lines (LuCaP 58 and LuCaP 136) did not exhibit any subcutaneous PAP immunoreactivity. LuCaP 86.2 and LuCaP 141 also exhibited strong immunoreactivity for PAP, LuCaP 35 displayed moderate PAP immunoreactivity, while LuCaP 70 and the neuroendocrine LuCaP 145.1 displayed either weak or no PAP expression in subcutaneous tumors.

Without being bound by theory, the disparity of PAP expression specifically for LuCaP 58 and LuCaP 136 between the intra-tibial and subcutaneous LuCaP tumors may show the role of the bone microenvironment's influence on tumor phenotypes including protein expression. CM isolated from subcutaneous tumor cells cultured in vitro for each of these xenograft lines was added to mouse MC3T3-E1 cells and of the eight lines, only LuCaP 23.1 induced mineralization (see FIG. 2A). As stated above, no PAP expression was observed in the osteoblastic LuCaP 58 and LuCaP 136 subcutaneous tumors. Mass spectrometry of the CM from each of the eight LuCaP subcutaneous tumors verified this by revealing that PAP was detected only in LuCaP 23.1 CM. Additionally, it was determined that LuCaP 23.1 CM also induced mineralization by human calvarial osteoblasts (HCO) in culture (p=0.0079) (see FIGS. 2B and 2C).

Example 10—LuCaP 23.1 CM Promotes Osteoblastic Gene Expression

Figure 3A:
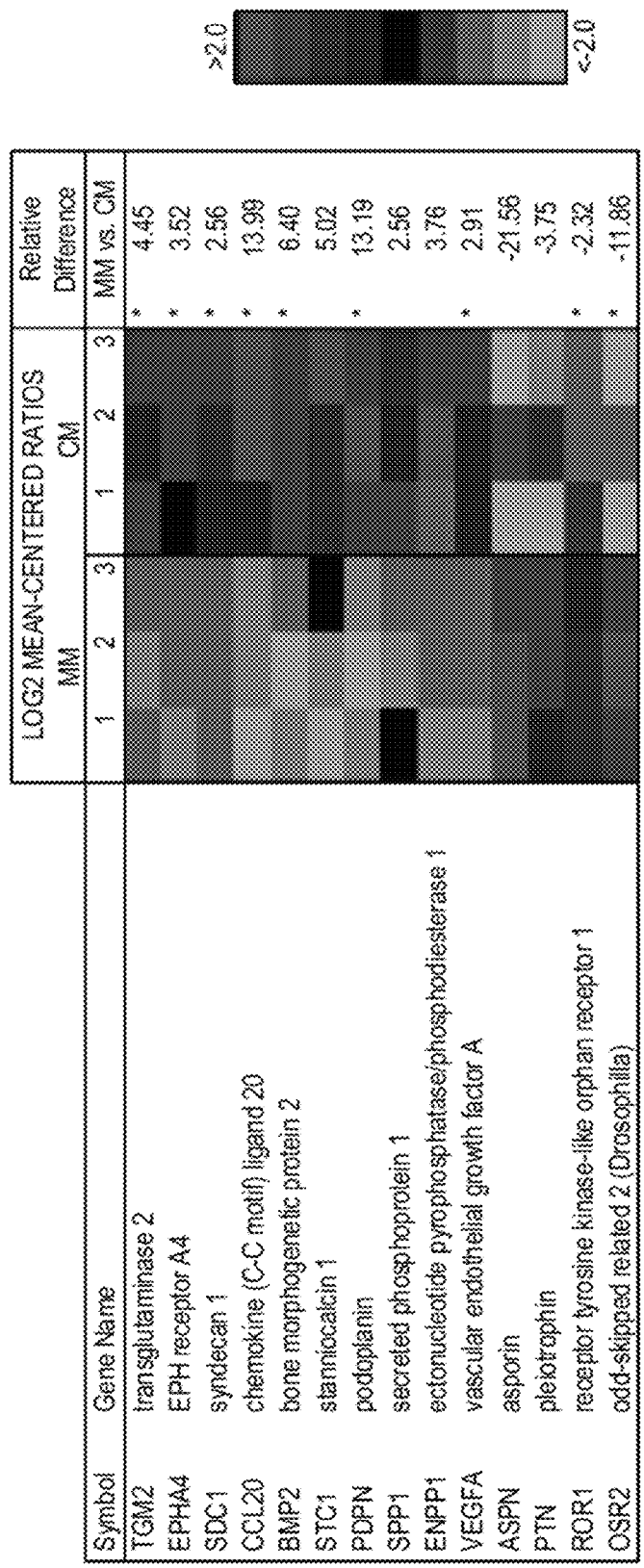
FIG. 3A depicts results from the use of AGILENT™ whole human genome microarrays to profile human bone marrow stromal cells (BMSC) from three donors in the presence of MM or LuCaP 23.1 CM, as indicated. Mean-centered ratios of 14 genes are colored according to scale (* probes returning significance in signal strength (p<0.05) using paired t-test).
Figure 3B:
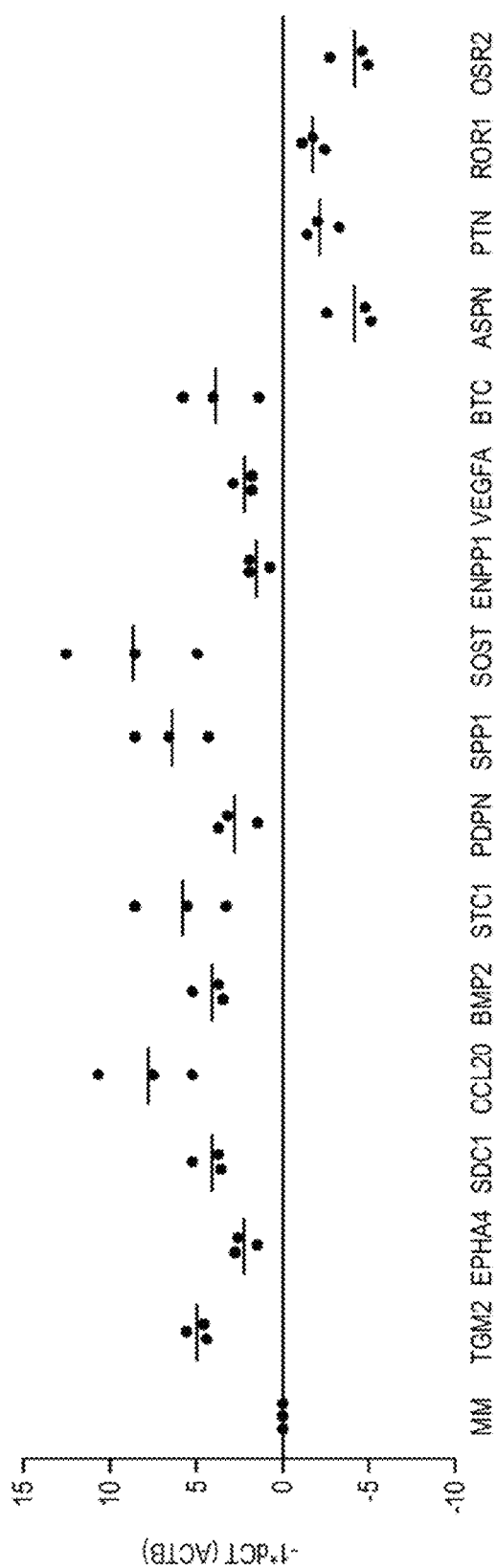
FIG. 3B is a graph depicting qRT-PCR validation for a subset of genes identified from the microarrays of FIG. 3A. All samples shown were normalized against β-actin and MM and all samples were significantly different from MM alone (p<0.05).

To evaluate the influence of PCa cells on BMSC, BMSC were exposed to MM or LuCaP 23.1 CM, RNA was extracted, and transcript levels were quantitated by microarray hybridization. Exposure to LuCaP 23.1 CM increased the expression of 174 genes and decreased the expression of 644 genes (q-value of 10%). 14 genes previously shown to be expressed in osteoblasts or involved in bone remodeling were selected for validation by qRT-PCR (see FIG. 3A) (see Feeley B T, et al. (2005) J Bone Miner Res 20:2189-2199; Kuroda C, et al. (2008) Biochem Biophys Res Commun 374:22-27; Kawai S, et al. (2007) J Bone Miner Res 22:1362-1372; Yoshiko Y, et al. (2003) Endocrinology 144: 4134-4143; Billiard J, et al. (2005) Mol Endocrinol 19:90-101; Dhodapkar M V, et al. (1998) Blood 91:2679-2688; Lisignoli G, et al. (2009) J Cell Physiol 221:154-160; Bijsterbosch J, et al. (2013) Osteoarthritis Cartilage 21:565-569; Kato K, et al. (2012) Proc Natl Acad Sci USA 109: 16876-16881; Erlandsen H, et al. (2012) J Histochem Cytochem 60:366-375; Seitz S, et al. (2013) Bone 53:231-238; Ariizumi T, et al. (2010) Pathol Int 60:193-202; and Clarkin C E, et al. (2013) Cell Biochem Funct 31:1-11). By qRT-PCR when normalized to MM alone, TGM2, EPHA4, SDC1, CCL20, BMP2, STC1, PDPN, SPP1, ENPP1, and VEGFA were significantly upregulated in the presence of LuCaP 23.1 CM (p<0.05), consistent with the gene expression array analysis (see FIG. 3B). Conversely, ASPN, PTN, ROR1, and OSR2 were significantly downregulated in the presence of LuCaP 23.1 CM (p<0.05), also consistent with the microarray analysis.

Example 11—PAP Induces Mineralization In Vitro

Figure 4B:
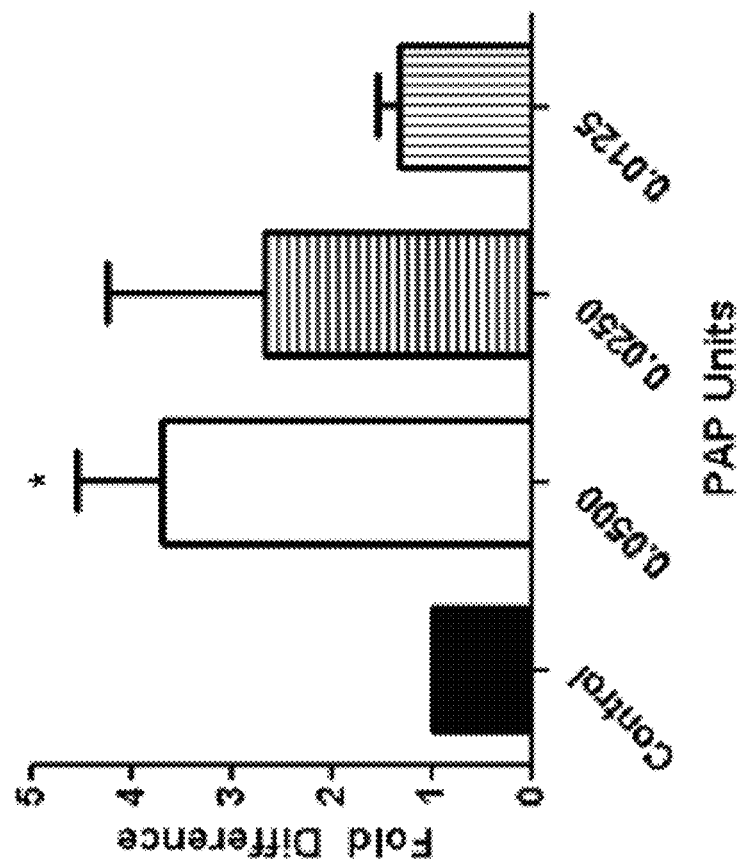
FIG. 4B is a graph depicting Alizarin Red staining of mineralization induced by PAP. Each experiment was repeated three times (* p=0.005).
Figure 4A:
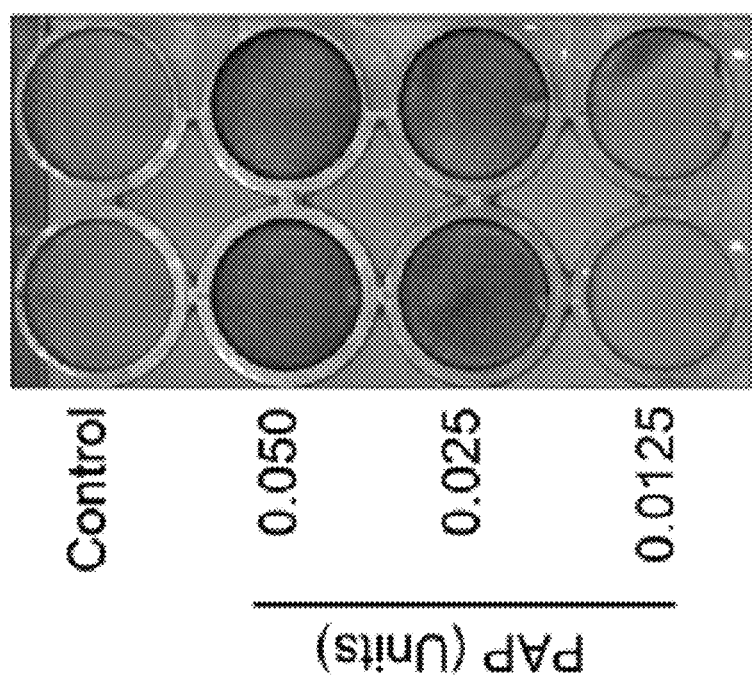
FIG. 4A depicts Alizarin Red staining showing that PAP induces mineralization in MC3T3-E1 cells.

High PAP levels were detected in LuCaP 23.1 CM. It was next determined if PAP contributes to mineralization induced by the LuCaP 23.1 CM. Mouse osteoblast-like MC3T3-E1 cells were treated with 0.05, 0.025, and 0.0125 units of PAP (see FIGS. 4A and 4B). Compared to control, 0.05 units of PAP treatment induced a significant 3.7 fold increase in mineralization (p=0.005).

Example 12—PA Blocks LuCaP 23.1-Induced Mineralization In Vitro

Figure 5B:
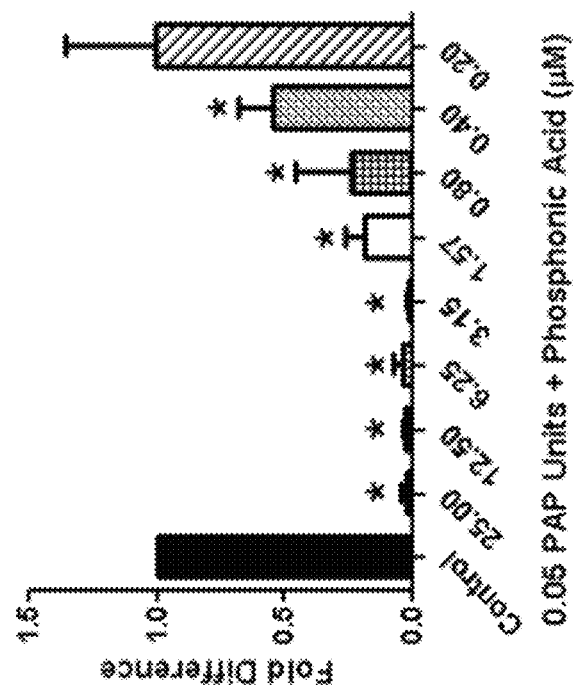
FIG. 5B is a graph showing that MC3T3-E1 cells treated with 0.05 units of PAP were inhibited by PA concentrations ranging from 25 µM to 0.4 µM, as indicated (* p<0.05).
Figure 5A:
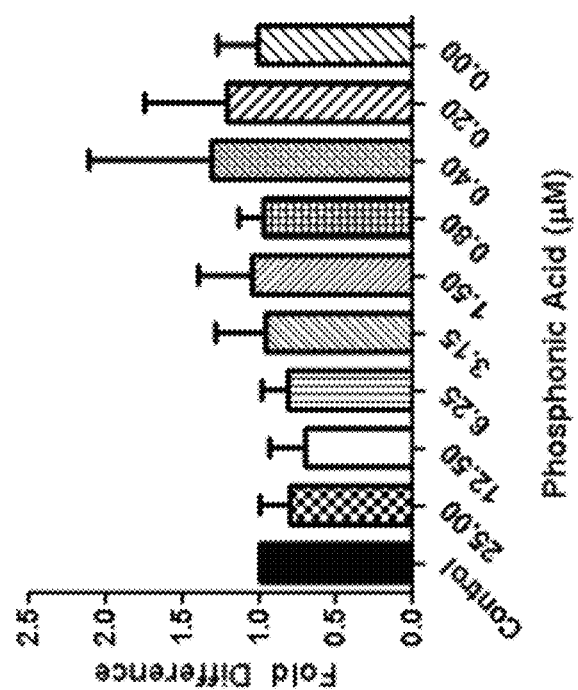
FIG. 5A is a graph showing that phosphonic acid (PA) has no significant effects on mineralization when added to MC3T3-E1 cells themselves at concentrations ranging from 25 µM to 0.2 µM, as indicated.
Figure 5C:
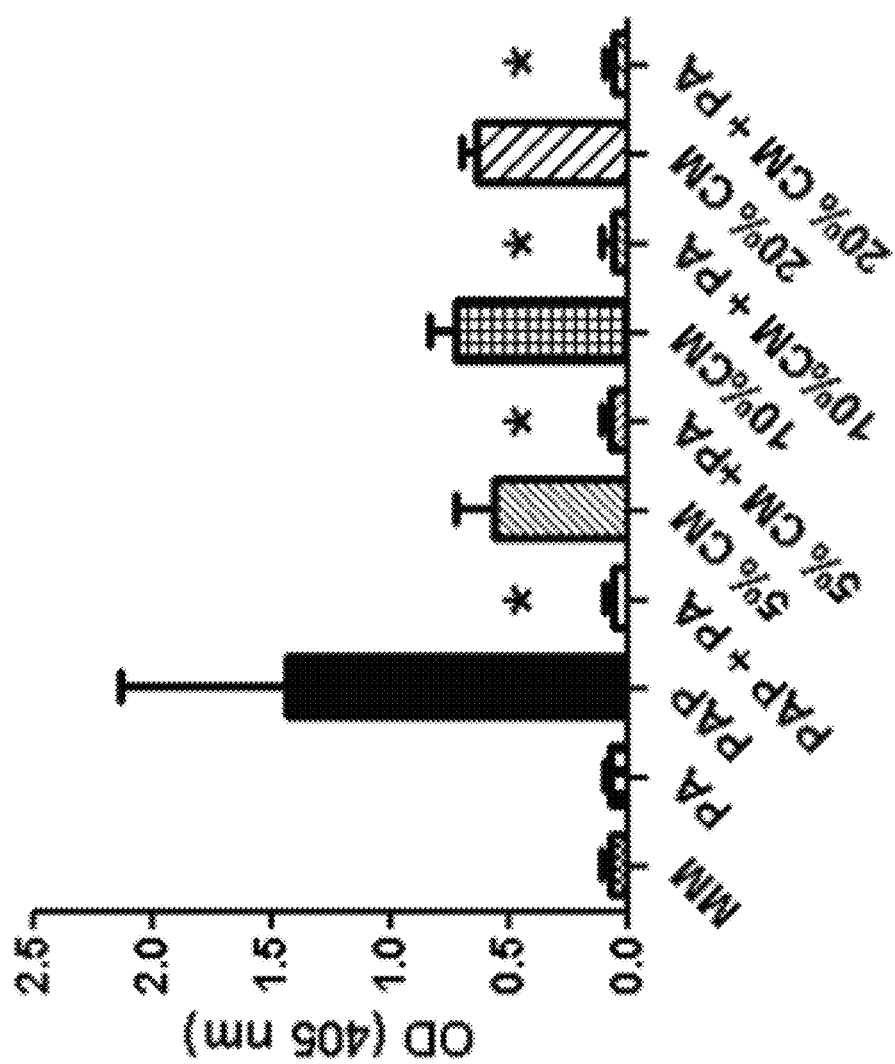
FIG. 5C is a graph showing that varying concentrations of LuCaP 23.1 CM (i.e., 5%, 10%, and 20%) uniformly reduced mineralization in the presence of 5 µM PA. Each experiment was performed three times (* p<0.05).

The benzylaminophosphonic acids are inhibitors of PAP (see Beers S A, et al. (1996) Bioorg Med Chem 4:1693-1701). Vovk, et al., have demonstrated that the R enantiomer of P-[phenyl[(phenylmethyl)amino]methyl]- is a potent inhibitor of PAP (see Vovk A I, et al. (2008) Bioorg Med Chem Lett 18:4620-4623). To determine if the PAP inhibitor P-phenyl[(phenylmethyl)amino]methyl]-(phosphonic acid; PA) has an indirect effect on MC3T3-E1 mineralization, PA was added to MC3T3-E1 cells at concentrations ranging from 25 μM down to 0.2 μM. No significant inhibition of mineralization occurred at 25 μM down to 0.2 μM (see FIG. 5A). Next, PA was added to MC3T3-E1 cells treated with 0.05 units of PAP at concentrations of PA ranging from 25 μM to 0.2 μM, to confirm its inhibitory potential. There was a dramatic reduction in mineralization in the 25 μM, 12.5 μM, 6.25 μM, and 3.15 μM concentrations of PA (decreasing mineralization by 97.6%, 95.6%, 92.1%, and 97.9%, respectively), with PA having a significant effect on mineralization down to 0.4 μM (see FIG. 5B). It was previously determined that 1% LuCaP 23.1 CM was not sufficient to induce mineralization in MC3T3-E1 cells and that 5% LuCaP 23.1 CM would promote mineralization in MC3T3-E1 cells. To determine if PA would reduce LuCaP 23.1 CM associated mineralization, MC3T3-E1 cells were treated with 5% to 20% LuCaP 23.1 CM with 5 μM PA. PA significantly reduced mineralization in MC3T3-E1 cells treated with 5%, 10%, or 20% LuCaP 23.1 CM, suggesting, without being bound by theory, that PAP is the active protein driving mineralization in LuCaP 23.1 CM (see FIG. 5C).

Example 13—PAP Expression is not Limited to Osteoblastic PCa Bone Metastases

Figure 6A:
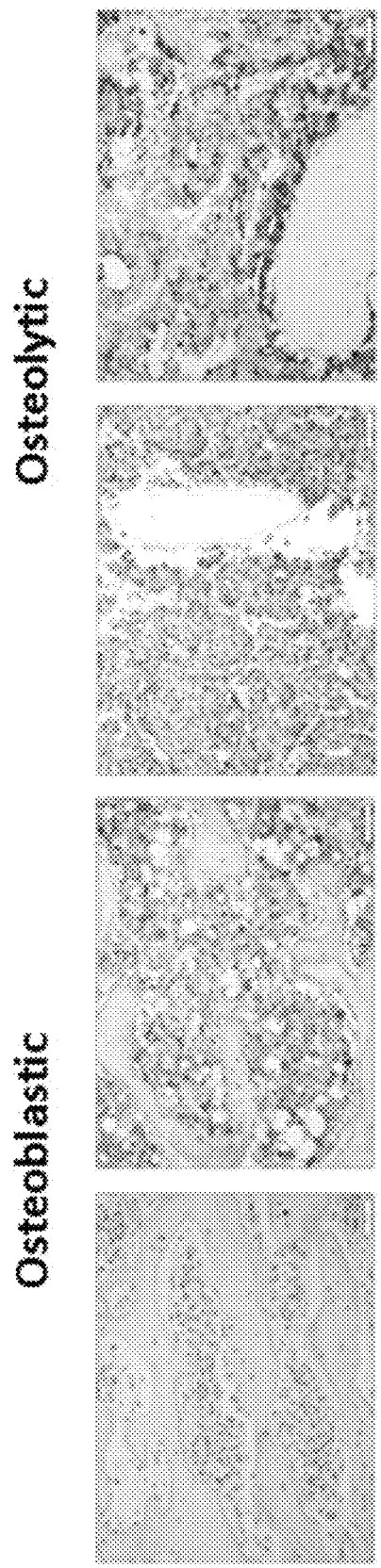
FIG. 6A is a series of images of representative immunohistochemistry (IHC) staining of PAP in osteoblastic and osteolytic PCa bone metastases, as indicated. The scale bars are equal to 50 µm.
Figures 6B, 6C:
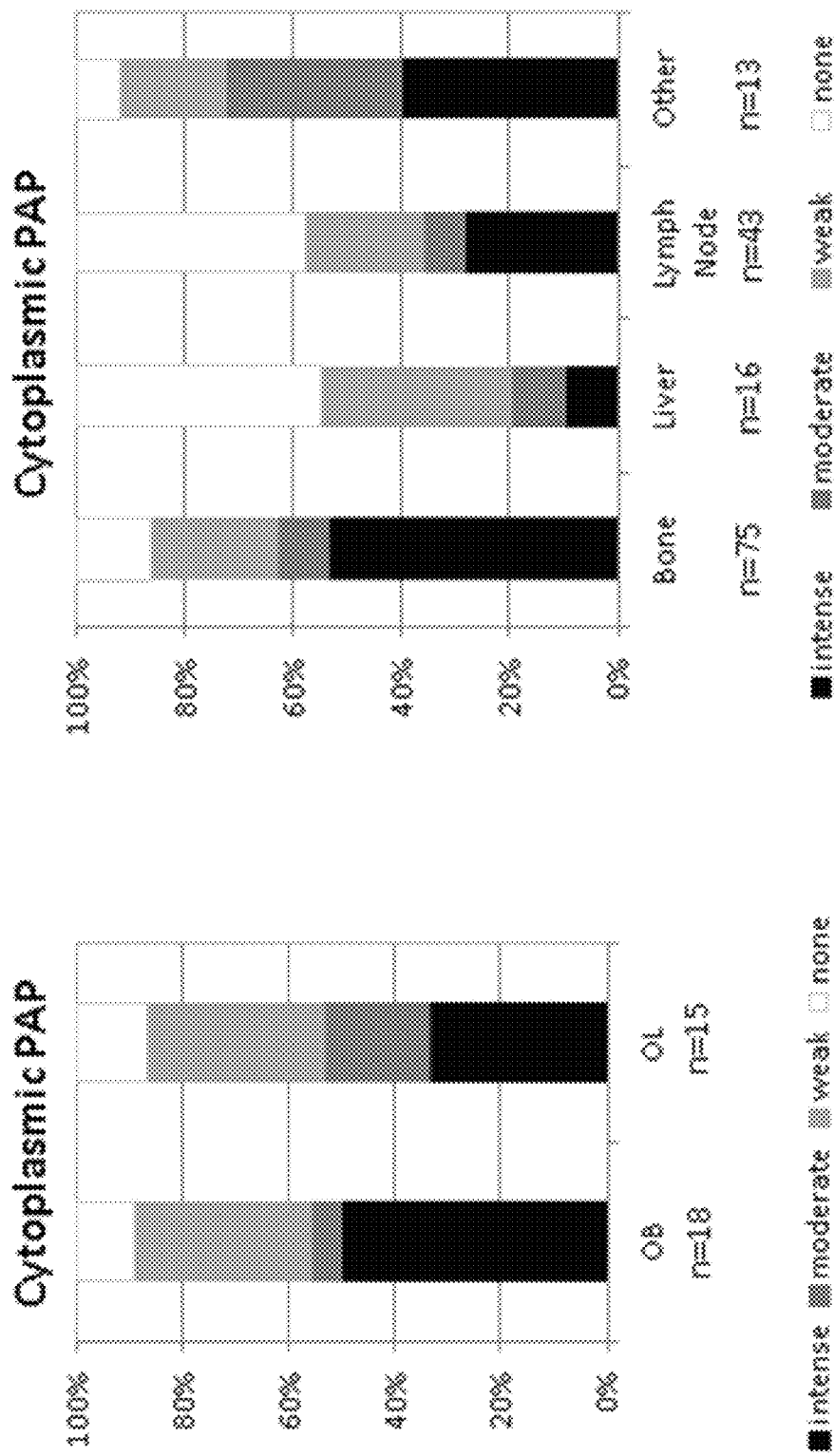
FIG. 6B is a graph showing that statistical analysis revealed no significant difference in the expression of PAP between the osteoblastic (OB) and osteolytic (OL) bone metastases (p=0.749). Staining intensity ranges from none (white) to intense (black).
FIG. 6C is a graph depicting statistical analysis of PAP expression in tumor metastases from bone, liver, lymph nodes, and other tissues (appendix, lung, and kidney). Expression of PAP was higher in bone metastases compared to other metastatic sites, such as liver (p<0.001) and lymph nodes (p<0.001), with no difference observed between bone and other tissues (appendix, lung, and kidney) (p=0.969).

PAP protein expression was analyzed by IHC from 30 patients in highly osteoblastic (n=18) or highly osteolytic (n=15) samples (see FIG. 6A), and shown to be expressed in 88% of the CRPC bone metastases. There was no significant difference between PAP expression in the osteoblastic versus osteolytic samples (see FIG. 6B). However, expression of PAP was higher in bone metastases compared to other metastatic sites, such as liver (p<0.001) and lymph nodes (p<0.001) with no difference observed between bone and other tissues (appendix, kidney, and lung) (see FIG. 6C). Furthermore, gene expression analysis and qRT-PCR results revealed that transcript levels of ACPP in seven highly osteoblastic and seven highly osteolytic clinical specimens, although present, displayed no significant differential expression between osteoblastic and osteolytic tissues (see FIGS. 7A and 7B).

Figure 7A:
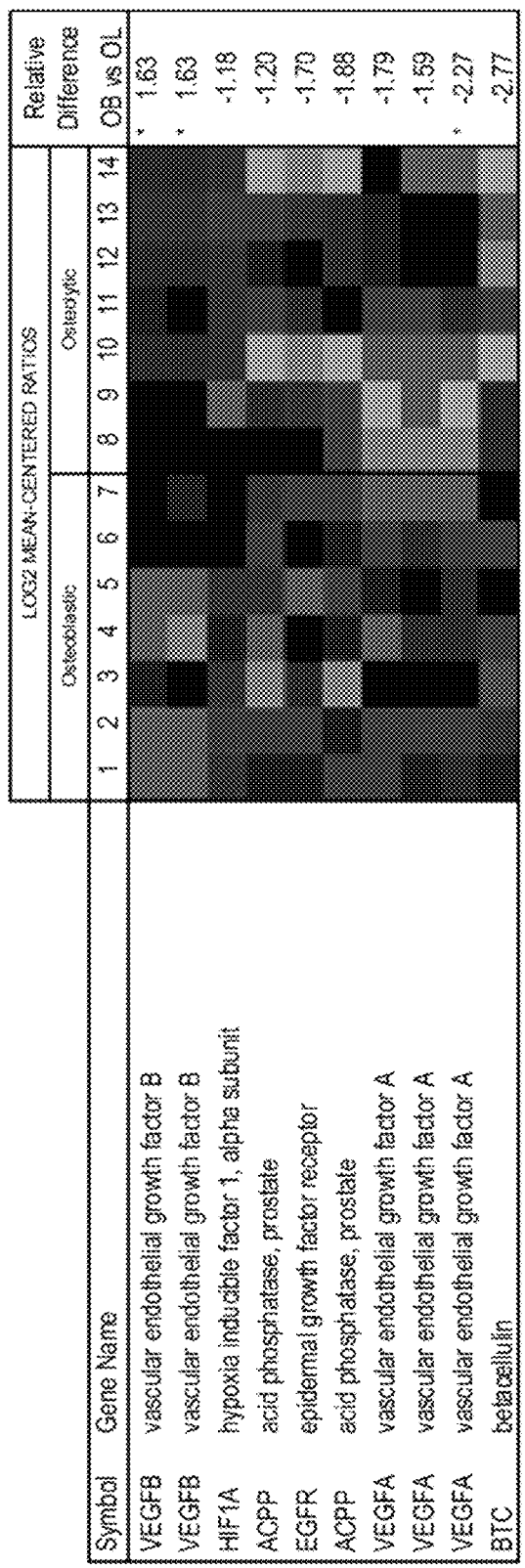
FIG. 7A depicts results from the use of AGILENT™ whole human genome microarrays to profile seven highly osteoblastic and seven highly osteolytic bone metastases. Mean-centered ratios of known and novel bone remodeling genes are colored according to scale (* probes returning significance in signal strength (p<0.05) using paired t-test).
Figure 7B:
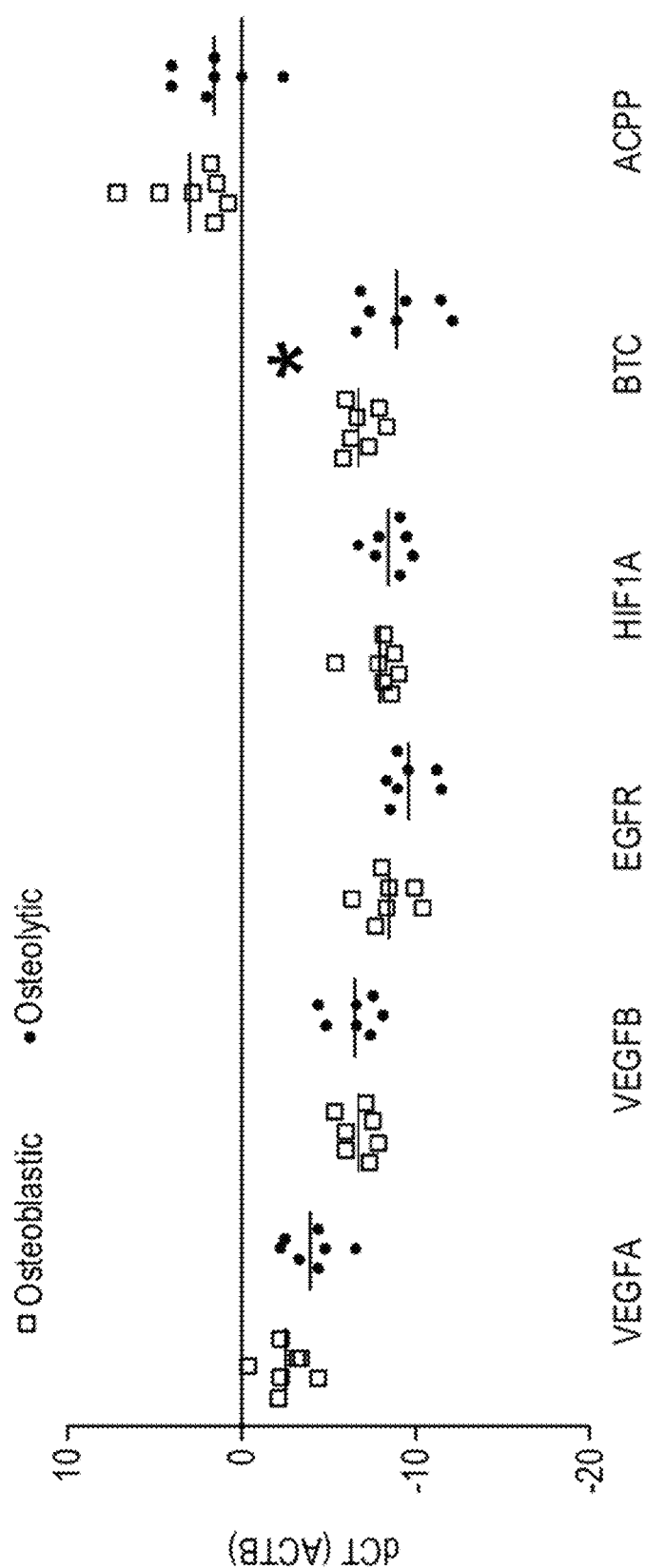
FIG. 7B is a graph depicting validation of the microarrays of FIG. 7A by qRT-PCR in osteoblastic (white squares) and osteolytic (black circles) PCa metastases. All samples are normalized against β-actin (* indicates significant difference with a p-value of p<0.05).

Example 14—Betacellulin is Associated with New Bone Formation in PCa Bone Metastases Gene expression array results and qRT-PCR from the patient samples (see FIGS. 7A and 7B) identified a novel bone formation-associated secreted factor, betacellulin (BTC), that could be responsible, at least in part, for the osteoblastic response in in vivo CRPC bone metastasis (see FIGS. 7A and 7B). Additionally, BTC was significantly upregulated over 8 fold in response to LuCaP 23.1 CM in vitro cultures (see FIG. 3B). Therefore, the expression of BTC-associated genes was also examined in the same samples. On the gene expression arrays, vascular endothelial growth factor A (VEGFA) and BTC were among the top secreted factors that were highly expressed in the osteoblastic versus osteolytic clinical metastases. Three other related factors, epidermal growth factor receptor (EGFR), vascular endothelial growth factor B (VEGFB), and hypoxia inducible factor alpha (HIFIA) were not differentially expressed on the gene expression arrays.

Figure 8:
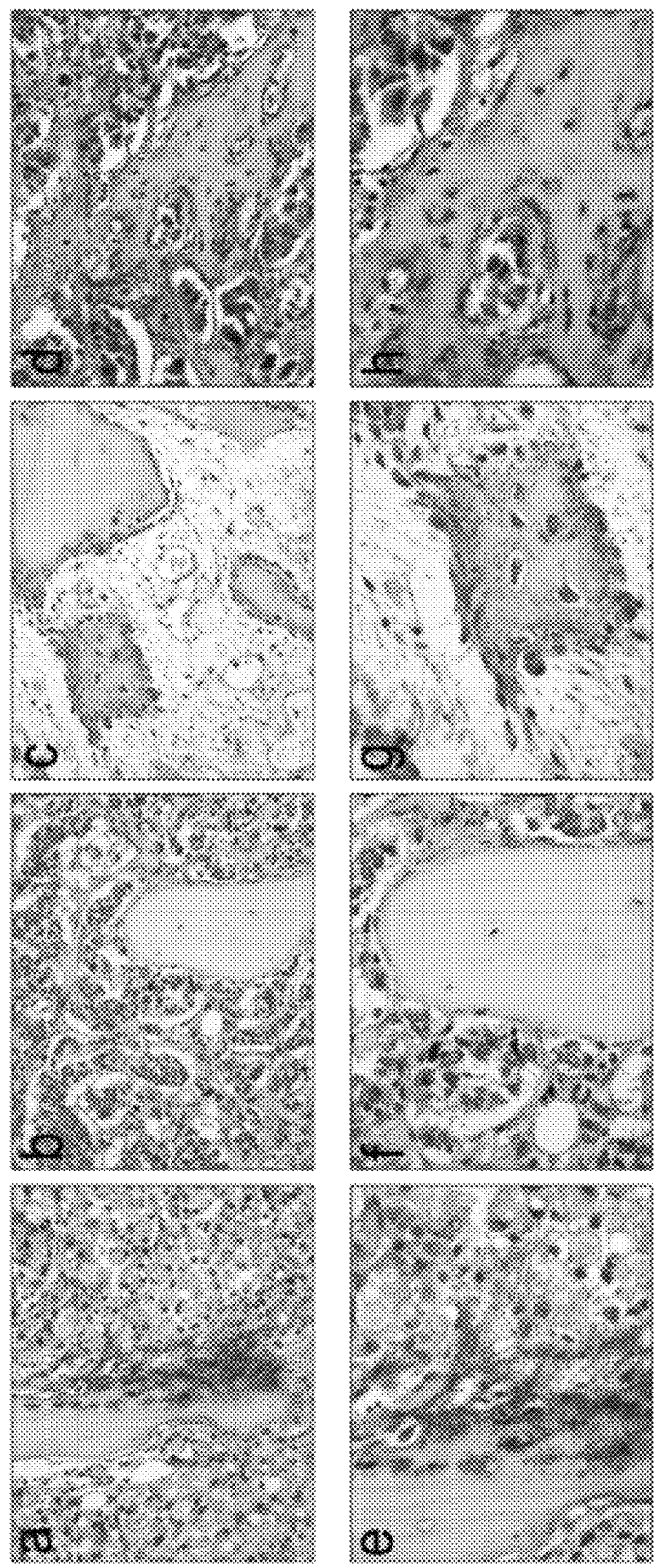
FIG. 8 is a series of images of clinical samples of PCa bone metastases. Panels "a" and "e" are images depicting new bone formation on older lamellar bone. Osteoblasts, osteocytes, and tumor stroma are strongly positive for BTC (dark black stain), while tumor cells stain weakly. Panels "b" and "f" are images of old lamellar bone in the center of a PCa bone metastasis. Limited BTC expression is observed in all cell types. Panels "c" and "g" are images of new bone formation in the reactive bone marrow stroma of an osteoblastic PCa bone metastasis. Osteoblasts and osteocytes are positive for BTC. Panels "d" and "h" are images showing that strong BTC expression is present in tumor cells, osteoblasts, osteocytes, and new bone. The magnification of panels "a" through "d" is ×200 and the magnification of panels "e" through "h" is ×400.

Using qRT-PCR, it was confirmed that VEGFA transcripts were upregulated in osteoblastic samples with a 2.77 fold increase, however, this only had a trend towards significance (p=0.067). BTC was significantly upregulated with a 4.26 fold increase (p=0.041) in osteoblastic metastases compared to osteolytic metastases. EGFR, VEGFB, and HIFIA transcript levels did not display any significant difference between osteoblastic and osteolytic samples by qRT-PCR (fold changes 2.19, 1.22, and 1.47, p=0.131, p=0.659, and 0.377, respectively). Upon further analysis of clinical CRPC bone metastases (n=36) by IHC, 15 metastatic sites with newly formed woven bone were identified in both osteoblastic and osteolytic samples. These new bones had eosinophilic staining in H&E sections, and consisted of a higher percentage of osteocytes than normal bone. By IHC, BTC expression was congruent with new bone formation, and was associated with osteoblasts, osteocytes, and was present at the new bone surface. Active stromal cells adjacent to the new bone also had similarly intense BTC staining. In contrast, the lamellar bone, from where the new bone was derived, was negative for BTC (see FIG. 8 and Table 2).

TABLE 2

| Sample ID | Bone Response | PCa cell Staining Intensity | New bone formation observed in the section | BTC staining on the new bone |
|---|---|---|---|---|
| 1 | OB | Moderate | None | N/A |
| 2 | OB | Moderate | None | N/A |
| 3 | OB | Intense | None | N/A |
| 4 | OB | None | Yes | Yes |
| 5 | OB | None | Yes | Yes |
| 6 | OB | None | Yes | Yes |
| 7 | OB | Intense | None | N/A |
| 8 | OB | None | None | N/A |
| 9 | OB | Moderate | Yes | Yes |
| 10 | OB | Weak | None | N/A |
| 11 | OB | Intense | None | N/A |
| 12 | OB | None | Yes | Yes |
| 13 | OB | Weak | None | N/A |
| 14 | OB | Weak | None | N/A |
| 15 | OB | None | Yes | Yes |
| 16 | OB | Weak | Yes | Yes |
| 17 | OB | None | Yes | Yes |
| 18 | OL | Intense | Yes | Yes |
| 19 | OL | None | Yes | Yes |
| 20 | OL | Intense | Yes | Yes |
| 21 | OL | Weak | None | N/A |
| 22 | OL | Moderate | Yes | Yes |
| 23 | OL | Weak | Yes | Yes |
| 24 | OL | Intense | None | N/A |
| 25 | OL | Weak | None | N/A |
| 26 | OL | Moderate | Yes | Yes |
| 27 | OL | Intense | None | N/A |
| 28 | OL | Weak | None | N/A |
| 29 | OL | Intense | None | N/A |
| 30 | OL | None | Yes | Yes |
| 31 | OL | Intense | None | N/A |
| 32 | OL | Moderate | None | N/A |
| 33 | OL | Weak | None | N/A |
| 34 | OL | None | None | N/A |

It will be apparent to those having skill in the art that many changes may be made to the details of the above-described embodiments without departing from the underlying principles of the invention. The scope of the present invention should, therefore, be determined only by the following claims.

The invention claimed is:

1. A method for treating a subject having an osteoblastic prostate cancer bone metastasis, comprising:
   administering to the subject a therapeutically effective amount of a pharmaceutical composition comprising a benzylaminophosphonic acid, a biologically active derivative of a benzylaminophosphonic acid, or a pharmaceutically acceptable salt, ester, solvate, isomer, or complex thereof.

2. The method of claim 1, wherein the benzylaminophosphonic acid is [phenyl[(phenylmethyl)amino]methyl]-phosphonic acid.

3. The method of claim 1, wherein the pharmaceutical composition is an inhibitor of prostatic acid phosphatase (PAP).

4. The method of claim 1, wherein the pharmaceutical composition reduces a pathological effect or symptom of the prostate cancer bone metastasis.

5. The method of claim 4, wherein the pathological effect or symptom of the osteoblastic prostate cancer bone metastasis is selected from at least one of bone pain, a bone fracture, spinal cord compression, and an increased blood calcium level.

6. The method of claim 1, wherein the subject has at least one of stage III prostate cancer, stage IV prostate cancer, and castration-resistant prostate cancer.

7. The method of claim 1, further comprising:
   identifying the subject having the osteoblastic prostate cancer bone metastasis.

8. The method of claim 1, wherein the subject is a human or a mammal.

9. A method for prophylactically treating a subject at risk of developing an osteoblastic prostate cancer bone metastasis, comprising:
   administering to the subject a therapeutically effective amount of a pharmaceutical composition comprising a benzylaminophosphonic acid, a biologically active derivative of a benzylaminophosphonic acid, or a pharmaceutically acceptable salt, ester, solvate, isomer, or complex thereof.

10. The method of claim 9, wherein the benzylaminophosphonic acid is [phenyl[(phenylmethyl)amino]methyl]-phosphonic acid.

11. The method of claim 9, wherein the pharmaceutical composition is an inhibitor of prostatic acid phosphatase (PAP).

12. The method of claim 9, wherein the pharmaceutical composition reduces the risk of developing the prostate cancer bone metastasis.

13. The method of claim 9, further comprising:
   identifying a subject having prostate cancer or at risk of developing an osteoblastic prostate cancer bone metastasis.

14. The method of claim 9, wherein the subject has at least one of stage III prostate cancer, stage IV prostate cancer, and castration-resistant prostate cancer.

15. The method of claim 9, wherein the subject is a human or a mammal.

16. A method for treating a pathological effect or symptom of an osteoblastic prostate cancer bone metastasis in a subject, comprising:
   administering to the subject a therapeutically effective amount of a pharmaceutical composition comprising a prostatic acid phosphatase (PAP) inhibiting agent, wherein the PAP inhibiting agent is selected from the group consisting of a benzylaminophosphonic acid, a biologically active derivative of a benzylaminophosphonic acid, and a pharmaceutically acceptable salt, ester, solvate, isomer, and complex thereof.

17. The method of claim 16, wherein the PAP inhibiting agent is [phenyl[(phenylmethyl)amino]methyl]-phosphonic acid.

* * * * *

UNITED STATES PATENT AND TRADEMARK OFFICE
CERTIFICATE OF CORRECTION

PATENT NO. : 9,682,090 B2
APPLICATION NO. : 14/941281
DATED : June 20, 2017
INVENTOR(S) : Colm Morrissey Page 1 of 1

It is certified that error appears in the above-identified patent and that said Letters Patent is hereby corrected as shown below:

In the Specification

Column 1, Line 17 reads, "Grant No. P50CA97186 . . ." which should read, "Grant No. P50CA097186 . . ."

Signed and Sealed this
Fifth Day of February, 2019

Andrei Iancu
*Director of the United States Patent and Trademark Office*

SEQUENCE LISTING

```
<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: PCR Primer

<400> SEQUENCE: 1
tctaggctcc aagggggtgt c                                          21

<210> SEQ ID NO 2
```

-continued

<211> LENGTH: 22
<212> TYPE: DNA
<213> ORGANISM: Artificial Sequence
<220> FEATURE:
<223> OTHER INFORMATION: PCR Primer

<400> SEQUENCE: 2
gtgctgcgtc tcattccgat ag                                            22

<210> SEQ ID NO 3
<211> LENGTH: 23
<212> TYPE: DNA
<213> ORGANISM: Artificial Sequence
<220> FEATURE:
<223> OTHER INFORMATION: PCR Primer

<400> SEQUENCE: 3
gcactcttcc agccttcctt cct                                           23

<210> SEQ ID NO 4
<211> LENGTH: 24
<212> TYPE: DNA
<213> ORGANISM: Artificial Sequence
<220> FEATURE:
<223> OTHER INFORMATION: PCR Primer

<400> SEQUENCE: 4
actcgtcata ctcctgcttg ctga                                          24

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
ttagcccttc acacatcgca ctga                                          24

<210> SEQ ID NO 6
<211> LENGTH: 24
<212> TYPE: DNA
<213> ORGANISM: Artificial Sequence
<220> FEATURE:
<223> OTHER INFORMATION: PCR Primer

<400> SEQUENCE: 6
atggaatgtt ggttgggact gagg                                          24

<210> SEQ ID NO 7
<211> LENGTH: 24
<212> TYPE: DNA
<213> ORGANISM: Artificial Sequence
<220> FEATURE:
<223> OTHER INFORMATION: PCR Primer

<400> SEQUENCE: 7
aggaggcaaa gaaaaggaac ggac                                          24

<210> SEQ ID NO 8
<211> LENGTH: 23
<212> TYPE: DNA
<213> ORGANISM: Artificial Sequence
<220> FEATURE:
<223> OTHER INFORMATION: PCR Primer

<400> SEQUENCE: 8

```
gggaagcagc aacgctagaa gac                                          23
```

<210> SEQ ID NO 9
<211> LENGTH: 24
<212> TYPE: DNA
<213> ORGANISM: Artificial Sequence
<220> FEATURE:
<223> OTHER INFORMATION: PCR Primer

<400> SEQUENCE: 9

```
ccaccacaca atcaaagcgg aaag                                         24
```

<210> SEQ ID NO 10
<211> LENGTH: 24
<212> TYPE: DNA
<213> ORGANISM: Artificial Sequence
<220> FEATURE:
<223> OTHER INFORMATION: PCR Primer

<400> SEQUENCE: 10

```
tcaactctct cacaccttgc tcca                                         24
```

<210> SEQ ID NO 11
<211> LENGTH: 24
<212> TYPE: DNA
<213> ORGANISM: Artificial Sequence
<220> FEATURE:
<223> OTHER INFORMATION: PCR Primer

<400> SEQUENCE: 11

```
ggcgaatcag aagcagcaag caac                                         24
```

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12

```
agtgaaacct ccaacccag caag                                          24
```

<210> SEQ ID NO 13
<211> LENGTH: 24
<212> TYPE: DNA
<213> ORGANISM: Artificial Sequence
<220> FEATURE:
<223> OTHER INFORMATION: PCR Primer

<400> SEQUENCE: 13

```
tgctggatga tagacgcaga tagt                                         24
```

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14

```
cagggcacgg tagaagttgg ag                                           22
```

<210> SEQ ID NO 15
<211> LENGTH: 25
<212> TYPE: DNA

<210> SEQ ID NO 15
<211> LENGTH: 25
<212> TYPE: DNA
<213> ORGANISM: Artificial Sequence
<220> FEATURE:
<223> OTHER INFORMATION: PCR Primer

<400> SEQUENCE: 15
tctttgttgg ctatggacct ggatt                                              25

<210> SEQ ID NO 16
<211> LENGTH: 25
<212> TYPE: DNA
<213> ORGANISM: Artificial Sequence
<220> FEATURE:
<223> OTHER INFORMATION: PCR Primer

<400> SEQUENCE: 16
ttatctctgg ggtttcttgt gaagg                                              25

<210> SEQ ID NO 17
<211> LENGTH: 23
<212> TYPE: DNA
<213> ORGANISM: Artificial Sequence
<220> FEATURE:
<223> OTHER INFORMATION: PCR Primer

<400> SEQUENCE: 17
cccaagcccc ataaccccta act                                                23

<210> SEQ ID NO 18
<211> LENGTH: 25
<212> TYPE: DNA
<213> ORGANISM: Artificial Sequence
<220> FEATURE:
<223> OTHER INFORMATION: PCR Primer

<400> SEQUENCE: 18
tttcatcagt gtctttgccc cagaa                                              25

<210> SEQ ID NO 19
<211> LENGTH: 22
<212> TYPE: DNA
<213> ORGANISM: Artificial Sequence
<220> FEATURE:
<223> OTHER INFORMATION: PCR Primer

<400> SEQUENCE: 19
caccactacc actgccacca ct                                                 22

<210> SEQ ID NO 20
<211> LENGTH: 25
<212> TYPE: DNA
<213> ORGANISM: Artificial Sequence
<220> FEATURE:
<223> OTHER INFORMATION: PCR Primer

<400> SEQUENCE: 20
catgttccat ttttcgcttt ctctg                                              25

<210> SEQ ID NO 21
<211> LENGTH: 23
<212> TYPE: DNA
<213> ORGANISM: Artificial Sequence
<220> FEATURE:
<223> OTHER INFORMATION: PCR Primer

<400> SEQUENCE: 21
tctgacgaag acgtggatct gct                                                23

-continued

```
<210> SEQ ID NO 22
<211> LENGTH: 23
<212> TYPE: DNA
<213> ORGANISM: Artificial Sequence
<220> FEATURE:
<223> OTHER INFORMATION: PCR Primer

<400> SEQUENCE: 22
ctccgacaaa aacccagtga gac                                              23

<210> SEQ ID NO 23
<211> LENGTH: 21
<212> TYPE: DNA
<213> ORGANISM: Artificial Sequence
<220> FEATURE:
<223> OTHER INFORMATION: PCR Primer

<400> SEQUENCE: 23
tgactccagg aaccagcgaa g                                                21

<210> SEQ ID NO 24
<211> LENGTH: 23
<212> TYPE: DNA
<213> ORGANISM: Artificial Sequence
<220> FEATURE:
<223> OTHER INFORMATION: PCR Primer

<400> SEQUENCE: 24
gcgaatgcct gttacactgt tga                                              23

<210> SEQ ID NO 25
<211> LENGTH: 23
<212> TYPE: DNA
<213> ORGANISM: Artificial Sequence
<220> FEATURE:
<223> OTHER INFORMATION: PCR Primer

<400> SEQUENCE: 25
gtgccctccc ttatgttgtt gga                                              23

<210> SEQ ID NO 26
<211> LENGTH: 24
<212> TYPE: DNA
<213> ORGANISM: Artificial Sequence
<220> FEATURE:
<223> OTHER INFORMATION: PCR Primer

<400> SEQUENCE: 26
ttggctttcc ttttcgttcc tgca                                             24

<210> SEQ ID NO 27
<211> LENGTH: 23
<212> TYPE: DNA
<213> ORGANISM: Artificial Sequence
<220> FEATURE:
<223> OTHER INFORMATION: PCR Primer

<400> SEQUENCE: 27
cacaatgccg aatgccagaa gac                                              23

<210> SEQ ID NO 28
<211> LENGTH: 25
<212> TYPE: DNA
<213> ORGANISM: Artificial Sequence
<220> FEATURE:
```

<223> OTHER INFORMATION: PCR Primer

<400> SEQUENCE: 28
tgctgatgtc cttttatgt tccac                                    25

<210> SEQ ID NO 29
<211> LENGTH: 23
<212> TYPE: DNA
<213> ORGANISM: Artificial Sequence
<220> FEATURE:
<223> OTHER INFORMATION: PCR Primer

<400> SEQUENCE: 29
tgaccttcac actccccaca cag                                     23

<210> SEQ ID NO 30
<211> LENGTH: 24
<212> TYPE: DNA
<213> ORGANISM: Artificial Sequence
<220> FEATURE:
<223> OTHER INFORMATION: PCR Primer

<400> SEQUENCE: 30
gctgccttcg tccttcttct tcat                                    24

<210> SEQ ID NO 31
<211> LENGTH: 24
<212> TYPE: DNA
<213> ORGANISM: Artificial Sequence
<220> FEATURE:
<223> OTHER INFORMATION: PCR Primer

<400> SEQUENCE: 31
ccagcaaccg aagttttcac tcca                                    24

<210> SEQ ID NO 32
<211> LENGTH: 24
<212> TYPE: DNA
<213> ORGANISM: Artificial Sequence
<220> FEATURE:
<223> OTHER INFORMATION: PCR Primer

<400> SEQUENCE: 32
tgcaccattc aactcctcgc tttc                                    24

<210> SEQ ID NO 33
<211> LENGTH: 25
<212> TYPE: DNA
<213> ORGANISM: Artificial Sequence
<220> FEATURE:
<223> OTHER INFORMATION: PCR Primer

<400> SEQUENCE: 33
tttccaaagg atgattgctg aggtg                                   25

<210> SEQ ID NO 34
<211> LENGTH: 24
<212> TYPE: DNA
<213> ORGANISM: Artificial Sequence
<220> FEATURE:
<223> OTHER INFORMATION: PCR Primer

<400> SEQUENCE: 34
ctgtctctga ttgtgctgac tgtg                                    24

```
<210> SEQ ID NO 35
<211> LENGTH: 23
<212> TYPE: DNA
<213> ORGANISM: Artificial Sequence
<220> FEATURE:
<223> OTHER INFORMATION: PCR Primer

<400> SEQUENCE: 35
ccagggtgac aagagcgaga tga                                                 23

<210> SEQ ID NO 36
<211> LENGTH: 24
<212> TYPE: DNA
<213> ORGANISM: Artificial Sequence
<220> FEATURE:
<223> OTHER INFORMATION: PCR Primer

<400> SEQUENCE: 36
tccttgatgg cacgaactgg aact                                                24

<210> SEQ ID NO 37
<211> LENGTH: 23
<212> TYPE: DNA
<213> ORGANISM: Artificial Sequence
<220> FEATURE:
<223> OTHER INFORMATION: PCR Primer

<400> SEQUENCE: 37
atggcagaag gaggagggca gaa                                                 23

<210> SEQ ID NO 38
<211> LENGTH: 22
<212> TYPE: DNA
<213> ORGANISM: Artificial Sequence
<220> FEATURE:
<223> OTHER INFORMATION: PCR Primer

<400> SEQUENCE: 38 cagggggcaca caggatggct tg                                                 22

<210> SEQ ID NO 39
<211> LENGTH: 22
<212> TYPE: DNA
<213> ORGANISM: Artificial Sequence
<220> FEATURE:
<223> OTHER INFORMATION: PCR Primer

<400> SEQUENCE: 39
gacatcaccc atcccactcc ag                                                  22

<210> SEQ ID NO 40
<211> LENGTH: 22
<212> TYPE: DNA
<213> ORGANISM: Artificial Sequence
<220> FEATURE:
<223> OTHER INFORMATION: PCR Primer

<400> SEQUENCE: 40
ggctcctctt tgttccccca ct                                                  22
```